(12) United States Patent
Adar et al.

(10) Patent No.: US 10,502,726 B2
(45) Date of Patent: Dec. 10, 2019

(54) METHOD AND SYSTEM FOR EXAMINING EGGS

(71) Applicant: LIVEGG (2015) LTD, R.d. Menashe (IL)

(72) Inventors: Yair Or Adar, Kvutzat Yavne (IL); Gavriel Adar, Kvutzat Yavne (IL); Eliahu Shalom Hoffman, Jerusalem (IL)

(73) Assignee: LIVEGG (2015) LTD, R.D. Menashe (IL)

( * ) Notice: Subject to any disclaimer, the term of this patent is extended or adjusted under 35 U.S.C. 154(b) by 0 days.

(21) Appl. No.: 16/387,869

(22) Filed: Apr. 18, 2019

(65) Prior Publication Data

US 2019/0277824 A1  Sep. 12, 2019

Related U.S. Application Data

(63) Continuation of application No. 15/123,140, filed as application No. PCT/IL2015/050309 on Mar. 24, 2015, now Pat. No. 10,267,780.

(Continued)

(51) Int. Cl.
*G01N 33/08* (2006.01)
*A01K 43/00* (2006.01)

(52) U.S. Cl.
CPC ........... *G01N 33/085* (2013.01); *A01K 43/00* (2013.01)

(58) Field of Classification Search
CPC ...... G01N 33/08; G01N 33/085; G01N 33/02; G01N 33/48; G01N 33/483;

(Continued)

(56) References Cited

U.S. PATENT DOCUMENTS

| 4,914,672 A | 4/1990 | Hebrank |
| 5,173,737 A | 12/1992 | Mitchell ............... A01K 45/00 356/53 |

(Continued)

FOREIGN PATENT DOCUMENTS

| CN | 1653329 A | 8/2005 |
| CN | 102907349 A | 2/2013 |

(Continued)

OTHER PUBLICATIONS

Lin Yang et al: "Noninvasive vasculature detection using laser speckle imaging in avian embryos through intact egg in early incubation stage", Biomedical Optics Express, vol. 4, No. 1, Dec. 10, 2012, pp. 32-37.

(Continued)

*Primary Examiner* — Gordon J Stock, Jr.
(74) *Attorney, Agent, or Firm* — Browdy and Neimark, P.L.L.C.

(57) ABSTRACT

A method and system are presented for use in examining an egg by monitoring radiation response from the egg during an incubation period. The monitoring comprises analyzing measured data indicative of the radiation response from the egg being detected at different time intervals of an incubation period, identifying predetermined dynamics in intensity variations of said radiation response during the different time intervals, and identifying in different time intervals presence of an alive embryo in said egg, and development stages and age of the embryo being developed.

2 Claims, 20 Drawing Sheets

Related U.S. Application Data

(60) Provisional application No. 61/969,334, filed on Mar. 24, 2014.

(58) Field of Classification Search
CPC ........... G01N 33/4833; G01N 21/4738; G01N 21/474; G01N 21/49; G01N 21/59; G01N 21/84; A01K 43/00; A01K 43/04; A01K 43/06; A01K 43/08; A01K 43/10
USPC ...................................................... 356/52–68
See application file for complete search history.

(56) References Cited

U.S. PATENT DOCUMENTS

| | | | |
|---|---|---|---|
| 5,745,228 A | 4/1998 | Hebrank et al. | |
| 5,898,488 A | 4/1999 | Kuhl | |
| 6,373,560 B1 | 4/2002 | Roux | |
| 6,535,277 B2 | 3/2003 | Chalker et al. | |
| 6,860,225 B2 | 3/2005 | Hebrank | |
| 7,333,187 B2 | 2/2008 | Hebrank | |
| 7,611,277 B2 | 11/2009 | Hebrank et al. | |
| 7,965,385 B2 | 6/2011 | Robert et al. | |
| 10,015,952 B2 * | 7/2018 | Adar | A01K 43/00 |
| 10,267,780 B2 * | 4/2019 | Adar | G01N 33/085 |
| 2005/0174824 A1 | 8/2005 | Reeves et al. | |
| 2005/0206876 A1 | 9/2005 | Reeves et al. | |
| 2006/0082759 A1 | 4/2006 | Hebrank | |
| 2007/0024843 A1 | 2/2007 | Hebrank et al. | |
| 2007/0024844 A1 | 2/2007 | Hebrank et al. | |
| 2008/0149033 A1 | 6/2008 | Hebrank et al. | |
| 2009/0091742 A1 | 4/2009 | Hebrank et al. | |
| 2009/0091743 A1 | 4/2009 | Hebrank et al. | |
| 2010/0141933 A1 | 6/2010 | Nadreau et al. | |
| 2011/0141455 A1 | 6/2011 | Adjanohoun et al. | |

FOREIGN PATENT DOCUMENTS

| | | |
|---|---|---|
| CN | 102960265 A | 3/2013 |
| FR | 2755580 A1 | 5/1998 |
| GB | 2166333 A | 5/1986 |
| JP | 2011106892 A | 6/2011 |
| RU | 2316208 | 2/2008 |
| RU | 2329642 | 7/2008 |
| WO | 02086495 A2 | 10/2002 |
| WO | 03096028 A2 | 11/2003 |
| WO | 09044243 A2 | 4/2009 |

OTHER PUBLICATIONS

MD. Hamidul Islam et al: Prediction of chick hatching time using visible transmission spectroscopy combined with partial least squares regression, Engineering in Agriculture, Environment and Food, vol. 8, No. 1, Oct. 22, 2014, pp. 61-66.

* cited by examiner

1600

1700

Live Embryo, Day 7

METHOD AND SYSTEM FOR EXAMINING EGGS

TECHNOLOGICAL FIELD AND BACKGROUND

The present invention, in some embodiments thereof, relates to the examination of eggs and, more particularly, but not exclusively, to a method and system for examining eggs, such as, but not limited to, poultry eggs.

In the poultry industry, in particular the chicken industry, discrimination between poultry eggs on the basis of some observable quality is a well-known and long-used practice. "Candling" is a common name for one such technique, a term which has its roots in the original practice of inspecting an egg using the light from a candle. As is known to those familiar with poultry eggs, although egg shells appear opaque under most lighting conditions, they are in reality somewhat translucent, and when placed in front of a direct light, the contents of the egg can be observed.

Candling operations have been done manually for many years. Automatic egg examining devices that utilize the transparency of the egg in order to differentiate between fertilized and unfertilized eggs have been developed over the years. These devices comprise emission means for emitting a light beam in the direction of an egg to be examined, receiving means for receiving the light beam passing through the egg, and means for processing data regarding the light beam received by the receiving means so as to determine the state of the egg. As a function of the level of absorption of the light beam passing through the egg, or the level of transparency of the egg, the data processing means can differentiate between fertilized eggs, i.e., eggs containing an embryo, and unfertilized eggs, including infertile eggs and rotten eggs. Some devices can also differentiate between live fertilized eggs containing a live embryo and dead fertilized eggs containing a dead embryo.

Conventional examining devices comprise a dispatch conveyor for transporting the eggs placed in their horizontal incubation racks or trays, emission means and receiving means being arranged on either side of the dispatch conveyor. In order to obtain satisfactory transparency measurements, the emitters and receivers are conventionally arranged opposite one another in the same vertical plane.

U.S. Pat. No. 6,373,560 discloses apparatus for candling eggs. The apparatus includes an incubation rack with an orifice, a transmission device with an luminous flux source aimed in a direction of the orifice in the incubation rack, a detection device positioned in alignment with the luminous flux source to receive luminous flux through the orifice, and an automatic analyzer connected to the detection device. The detection device and the transmission device are arranged in a substantially vertical plane, one beneath the orifice and the other above the orifice. The apparatus also includes a protection screen for protecting the transmission device or the detection device against smears originating from eggs or the incubation rack.

U.S. Pat. No. 5,898,488 discloses trays of eggs filled with candled eggs wherein infertile eggs are removed from trays of fertile eggs and are replaced with fertile eggs in order to supply a complete array of fertile eggs within the tray.

U.S. Pat. No. 5,745,228 discloses apparatus for distinguishing live from infertile poultry eggs. The apparatus comprises an egg carrier, a light measuring system having a light source positioned on one side of the egg carrier and a light sensor positioned on the other side of the egg carrier opposite the light source, and a switching circuit for cycling the intensity of the light source at a frequency greater than 100 cycles per second.

U.S. Patent Application Publication No. 20100141933 discloses an automatic egg examining device for differentiating between fertilized and unfertilized eggs. The device comprises means for emitting a light beam in the direction of the egg to be examined, means for receiving the light beam passing though the egg, and means for processing data regarding the received light beam in order to determine the fertilized or unfertilized state of the egg. The emission means comprise, for each egg, at least one coherent laser source forming a coherent optical beam in the direction of the egg.

U.S. Patent Application Publication No. 20070024843 discloses a method of candling eggs. An egg is illuminated with light from a light source, and light passing through the egg is received at a light sensor. An output signal that corresponds to the received light is generated and analyzed to determine whether the optical path between the light source and light sensor has been altered.

U.S. Pat. No. 6,535,277 discloses a method of non-invasively identifying a present condition of an egg. The egg is illuminated with light from a light source and light passing through the egg is received at a sensor positioned adjacent the egg. The intensity of the received light at a plurality of the visible and infrared wavelengths is determined, and a spectrum that represents light intensity at selected wavelengths is generated. The generated spectrum is compared with a spectrum associated with a known egg condition.

Great Britain Patent No. GB2166333 discloses a machine for candling eggs. The machine comprises light measuring systems, each including a light source and a sensor. The light measuring systems are arranged such that the eggs are shielded relative to each other.

Additional background art include U.S. Pat. Nos. 4,914.672, 5,745,228, 6,860,225, 7,333,187, 7,611,277 and 7,965,385, U.S. Patent Application Publication Nos. 2005/0206876, 2006/0082759, 2007/0024843, 2007/0024844, 2008/0149033, 2009/0091742, 2009/0091743, 2011/0141455, and International Publication Nos. WO/2003/096028, WO/2002/086495, WO/2003/096028 and WO/2009/044243.

GENERAL DESCRIPTION

There is a need in the art in a novel approach for monitoring the incubation process of eggs, enabling early diagnosis of the egg/embryo viability conditions and accordingly enabling for optimizing environmental conditions of the incubation process and throughput.

The present invention provides a novel method and system for use in examining egg(s), enabling monitoring the incubation process. The invention provides for analyzing measured data indicative of continuously or periodically detected radiation response from one or more regions of interest each including one or more eggs and determining dynamics in variation of the radiation response during different successive time intervals of the incubation period. The analysis of such a time pattern of the detected optical data provides for sequential evaluation of such events as presence of an alive embryo in the egg, and further development stages and age of the embryo being developed.

According to a first broad aspect of the invention, there is provided a method of examining an egg, the method comprising monitoring radiation response from the egg during an incubation period, the monitoring comprising analyzing measured data indicative of the radiation response from the egg being detected at different time intervals of an incubation period, identifying dynamics in intensity variations of said radiation response during the different time intervals, and identifying in the different time intervals presence of an alive embryo in said egg, development stages and age of the embryo being developed.

The monitoring may comprise receiving data, indicative of the radiation response detected from the egg while in an incubator (on-line mode), or from a storage device where such data has been previously stored (off-line mode). The received data may comprise a plurality of data pieces, each corresponding to the measured radiation response from different egg(s) at a different site in the incubator, thereby enabling to obtain a map (distribution) of the dynamics in intensity variations of said radiation response during the different time intervals within the incubator. The map data can be analyzed to generate data about environmental conditions within the incubator, thereby enabling adjustment of said conditions. In some embodiments, the dynamics in the intensity variations of the radiation response during the different time intervals comprise at least one of the following: a change in a frequency of the intensity variations at different time intervals, appearance and disappearance of a certain frequency of the intensity variation, and a change in an amplitude of the intensity varying at a certain frequency.

In some embodiments, the analyzing of the measured data comprises: analyzing first measured data indicative of the radiation response being monitored within an initial time interval of the incubation period of up to 7 days, and upon identifying a predetermined first pattern of the variation of intensity of the radiation response being indicative of the alive embryo in said egg, generating data indicative thereof allowing to proceed said monitoring for a successive time interval of the incubation period. In this connection, it should be understood that sometimes, upon identifying absence of the predetermined first pattern in the initial time interval for a specific egg, corresponding data can be generated to stop monitoring of this specific egg.

In some embodiments, the analyzing of the measured data further comprises analyzing second measured data indicative of the radiation response being monitored during said successive time interval, to identify predetermined dynamics in variation of the intensity of the radiation response, to thereby enabling selectively stop the monitoring after a first time window of said successive time interval or proceed with the monitoring during a further second time window of said successive time interval. In some embodiments, the first time window of the successive time interval may be selected to determine whether said variation of the intensity of the radiation response is indicative of that the alive embryo in said egg is maintained, to thereby allow said monitoring to proceed to the second time window, to monitor development of the embryo based on identification of predetermined dynamics in time variation of intensity of the radiation response.

In some embodiments, the predetermined first pattern of the variation of intensity of the radiation response in said first measured data comprises a variation frequency in a range of 0.1-1 Hz. The predetermined first pattern having periodic variations at a frequency equal or less than 1 Hz (e.g. 0.5 Hz) may be indicative of the alive embryo in the egg. The first pattern may be identifiable at a fifth day of the incubation period. The radiation response obtained during the initial time interval may be indicative of a breathing effect.

In some embodiments, the radiation response obtained during the successive time interval comprises variation of the intensity of the radiation response with frequencies in a frequency range of 2-4 Hz. The dynamics of the intensity variation may be such that the first pattern appears, becomes stronger (better defined periodicity), and then disappears being masked by the second pattern of 2-4 Hz frequency of the intensity variation. Then, the second pattern, while maintaining the 2-4 Hz frequency range of variation, becomes characterized by increasing amplitude of the signal. Thus, in some embodiments, the analysis of the second measured data comprises identifying a change in a frequency of the intensity variation during the first time window of the successive time interval as compared to that of the initial time interval, and identifying a change at least in the amplitude of the radiation response during the second time window as compared to that of the first time window of the successive time interval. The analysis of the second measured data may further comprise identifying a change in periodicity of the intensity variation within a predetermined frequency range during the successive time interval as compared to that of the initial time interval. The analysis of the second measured data may further comprise identifying a change in periodicity of the intensity variation in the first time window of the successive time interval as compared to that of the initial time interval. The analysis of the second measured data may comprise identifying continuing increase of amplitude in the intensity variation with frequencies in the range of 2-4 Hz from eleventh day of the incubation period.

In some embodiments, the predetermined first pattern may be indicative of presence of the embryo in the egg at an age of from about 6 days to about 11 days.

In some embodiments, the monitoring of the radiation response from the egg may comprise illuminating the egg with electromagnetic radiation of a predetermined spectral range, detecting the radiation response from the egg formed by radiation reflected from the interior of the egg; and generating the measured data indicative of the detected radiation response.

In some embodiments, the above-described monitoring procedure may be executed simultaneously for at least two eggs, each egg being positioned in a different tray of an incubator. It should be noted that the illuminating and detecting of the radiation may be carried in a non-contact fashion (i.e. light source and light sensor are spaced from the egg) and may be carried out in either or both of transmission and reflection modes of the radiation detection (by appropriate accommodation of the light source and light sensor and their associated light directing optics defining the orientation of the illumination and detection channels with respect to the egg). The illuminating may be executed in pulses, e.g. with the pulse duration of less than 30 microseconds. The radiation may be monochromatic, may comprise one or more wavelengths in the infrared spectral range, may be in a range from about 600 nm to about 1550 nm.

The illumination and detection of the radiation response (i.e. measurement) is performed continuously or periodically. For example, the measurement(s) is/are performed every hour with the measurement duration of about 1 minute. To this end, the measurement unit (optical unit) and/or the monitoring system includes a controller for operating the time pattern of the measurement sessions.

In some embodiments, the analyzing of the measured data may further comprise identifying malposition of the embryo in the egg, based on said intensity variations. In some embodiments, the analyzing of the measured data may further comprise identifying malformation of an embryo in the egg, based on said intensity variations.

In some embodiments, the analyzing of the measured data may further comprise predicting a hatching time of the egg based on appearance and disappearance of said intensity variations.

The method may further comprise generating data for adjusting at least one environmental parameter in an incubator containing the egg, responsively to the predicted hatching time.

According to another broad aspect of the invention, there is provided a monitoring system for use in examining an egg, the system comprising: data input utility configured for receiving measured data indicative of radiation response detected from the egg during an incubation period; and a control unit configured and operable for analyzing the measured data, said analyzing comprises identifying dynamics in intensity variations of said radiation response during different time intervals of the incubation period, and identifying, in different time intervals, presence of an alive embryo in said egg, development stages and age of the embryo being developed.

The system may further comprise an optical unit configured and operable for illuminating a region of interest with electromagnetic radiation of a predetermined spectral range, detecting the radiation response from an interior of an egg while located in said region of interest, and generating the measured data indicative of the detected radiation response. The optical unit may comprise a light source and a light sensor, which are spaced from said region of interest, and the optical unit may be configured for operation in either or both of transmission and reflection modes of the radiation detection. The light source and the light sensor may be mounted on a planar board. In some embodiments, the optical unit is configured for the detection of the radiation response from more than one regions of interest inside an incubator.

The system may further comprise a controller configured for operating said optical unit to provide illuminating radiation in pulses. According to yet another broad aspect of the invention, there is provided an incubator system, comprising: a housing for accommodating eggs; a heater for heating an interior of said housing; at least one tray within the housing, for supporting said eggs; and the system described above, wherein the optical unit is positioned inside the housing in at least one of the following configurations: above the tray, below the tray, or inside said tray.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF EMBODIMENTS

Figure 1A:
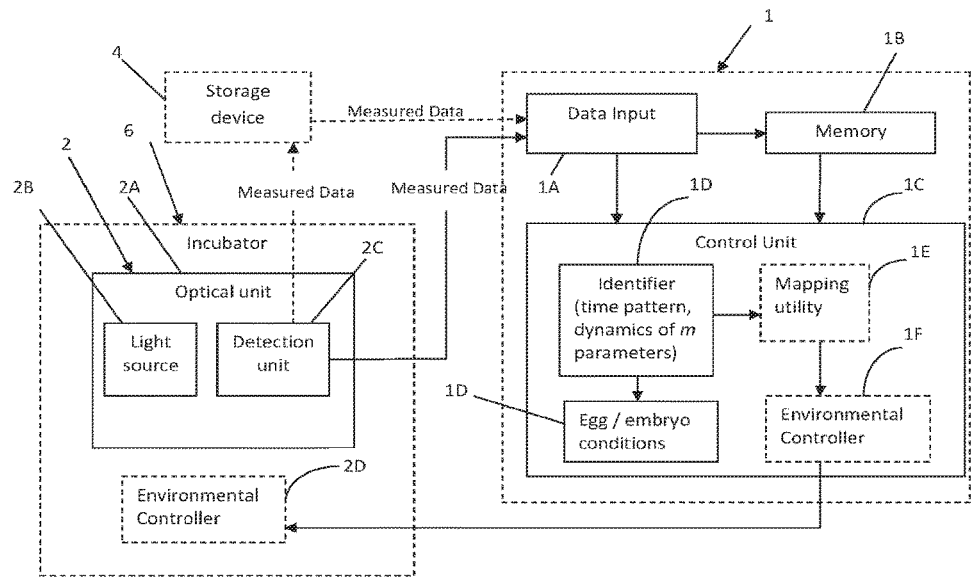
FIG. 1A is a block diagram of a monitoring system of the invention for use in examining egg(s), enabling optimization of the incubator operation.

The present invention in general relates to the examination of eggs and, more particularly, but not exclusively, to a method and system for examining eggs, such as, poultry eggs during an incubation period.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
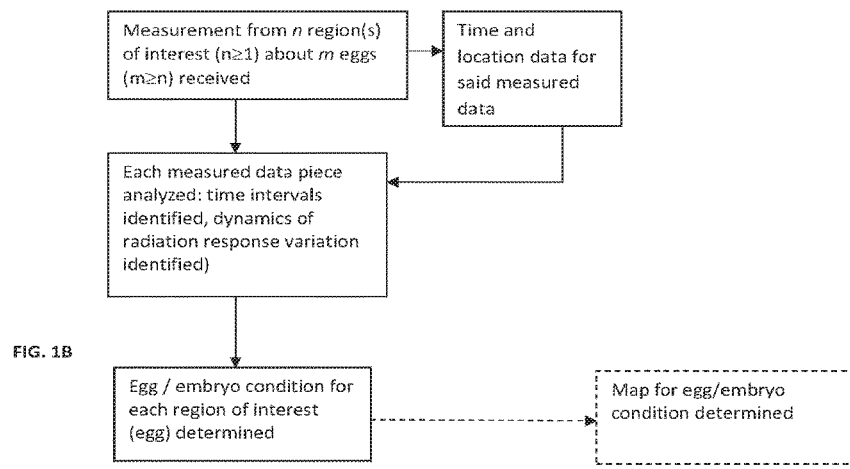
FIG. 1B is a flow diagram exemplifying a method of the invention for monitoring the egg/embryo conditions.

Reference is made to FIGS. 1A and 1B schematically illustrating the principles of the invention. FIG. 1A illustrates, by way of a block diagram, a monitoring system 1 configured for use in examining one or more eggs. FIG. 1B illustrates a method, performed by system 1, for monitoring the eggs' conditions.

It is to be understood that, unless otherwise defined, the operations described herein below can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The egg to be examined is preferably a poultry egg, including, without limitation, a chicken egg, a turkey egg, a quail egg, a duck egg, a goose egg, an ostrich egg, an egg from a game bird (e.g., pheasant, partridge) or the like. In some embodiments of the present invention the egg is a chicken egg. The egg is optionally and preferably a commercial egg, obtained from parent stock (also referred to as breeder stock). Commercial eggs are those eggs that yield commercial poults or chicks that are grown and used for meat production. In some embodiments the egg is one of those used to produce the parent stock. For example, the egg can be produced by grandparent stock, great grandparent stock, or great grandparent stock, etc.

The monitoring system 1 of the invention is configured as a computer system including inter alia such utilities (software/hardware utilities) as data input utility 1A which may be associates with suitable communication ports for receiving data via wires or wireless signal transmission (e.g. via communication network); memory 1B, and control unit (processor) 1C. The processor 1C is configured according to the invention for processing measured data received via the input 1A and generating data about egg/embryo conditions, as will be described more specifically further below.

The monitoring system may receive measured data directly from a measuring unit 2, which is typically an optical unit, and can thus operate in a so-called on-line (real time) mode for analyzing the data being measured. Alternatively, or additionally, the monitoring system may receive measured data from a storage device 4 where such data has been previously stored during the measurements, and can thus perform the data analysis in a so-called off-line mode. As shown in the figure, the optical unit 2 may be configured for accommodation inside an incubator 6. The optical unit includes a light source unit 2A and a detection unit 2B. It should be noted that the light source unit, as well as a detection unit inside the incubator may be constituted by appropriate light output and light input ports respectively, while light emitter and light sensor may be mounted outside the incubator and connected to the respective ports via optical guiding means. It should also be noted that the monitoring system 1 may actually be an integral part of the detection unit.

The control unit 1C (data processor) comprises an identifier module (software) which receives and analyzes the measured data. The measured data is indicative of a radiation response of a region of interest, where one or more eggs are located, to predetermined illumination. In this connection, the following should be understood. The optical unit (its light source unit) includes appropriate light directing and focusing optics for illuminating the interior of the egg and receiving the radiation response thereof. i.e. transmission of the illumination through the egg and/or reflection of the illuminating light from the interior of the egg. In other words, the optical unit, i.e. its illumination and detection channels, may be configured for operation in either one or both of transmission and reflection modes. Further, the optical unit may be configured for concurrently or sequentially illuminating/detecting radiation from a plurality of sites (constituting region of interests) in the incubator. For example, the optical unit may operate in a scanning mode or may define several illumination and detection channels. The optical unit may be associated with (i.e. include or connectable to) a controller which operates a time pattern (sequence) of measurement sessions on each site (egg). Such a measurement controller may be part of the monitoring system, in case of the real time monitoring mode.

Thus, the measured data may generally include n data pieces including information about n regions of interest, where n≥1, where each region of interest may include m eggs, where m≥n. Generally, the measured data may be configured with data piece per egg, or data piece per region of interest including one or more eggs. Considering concurrent or sequential monitoring of multiple eggs/regions of interest, input data into the control unit also includes location data in correspondence with the measured data pieces.

The control unit 1C optionally further includes a mapping utility 1E which receives time pattern data and location data of the measured data pieces and generates map data corresponding to the various measurement times and the location of each measurement. The map data may be then used to evaluate distribution of the effect of environmental conditions within the incubator on the embryo development, and enables to generate instructions to modify, as the need may be, environmental conditions inside the incubator. For this, the mapping utility 1E may communicate with an environmental controller module 1F, by sending to it the modification instructions about the environmental conditions to be executed, and the environmental controller module transfers the modification instructions to an environmental controller utility 2D, located within the incubator, that executes the changes in the environmental conditions.

Further, the identifier 1D may plot and present data about the egg or embryo condition based on analysis performed on the measured data during the various time intervals of the incubation period, as will be described further below. To this end, the system or the control unit may include a display utility (not shown) for presenting the analysis results and data about the egg or embryo conditions, such as indicating that an egg in a certain region of interest is empty, or that the embryo in a specific egg is alive.

FIG. 1B illustrates in more details the flow of operations that are executed by the identifier 1D and the mapping utility 1E of the control unit 1C. The identifier 1D receives measured data which includes measurements from n region(s) of interest about m eggs, together with the corresponding time (incubation stage) and location data for each measurement, i.e. for each egg in each region of interest. Thus, measured data includes one or more data pieces, each formed by the measurement (radiation response), time and location. Each measured data piece is analyzed.

The analysis includes identification of different time intervals of the detection of the radiation response, and identification and evaluation of the dynamics of radiation response variation. The dynamics of radiation response variation include at least one of the following: a change in a frequency of the intensity variations at different time intervals, appearance and disappearance of a certain frequency of the intensity variation, and a change in amplitude of the intensity varying at a certain frequency.

For example, the analysis of the measured data may include analyzing first measured data indicative of the radiation response being monitored within an initial time interval of up to 7 days of the incubation period. Upon identifying a predetermined first pattern of the intensity variation being indicative of the alive embryo in the egg, the identifier may generate corresponding data which allows to proceed with the monitoring for a successive time interval of the incubation period. For example, the monitoring procedure is performed periodically, e.g. about 1 minute monitoring every hour.

The inventors have found that in early stages of the incubation, e.g. around the fifth day, the predetermined first pattern of the intensity variation may be characterized by the variation frequency in the range of 0.1-1 Hz, which may indicate movements inside the egg which might be indicative of the start of breathing. Then, a second measured data indicative of the radiation response being monitored during the successive time interval is analyzed in order to identify predetermined dynamics in intensity variation. Based on the identified dynamics, the monitoring may be selectively stopped after a first time window of the successive time interval or proceed for a further second time window of successive time interval. If the embryo is diagnosed as alive, then analysis may be performed on the data in the first and second time windows of the successive time interval, and development stages of the embryo may be acquired according to predetermined dynamics in intensity variation of the radiation response. The variation of the intensity of the radiation response in the successive time interval may include periodic signals with a frequency range of 2-4 Hz, which may be attributed to heart beat. The heart beat signal may appear in a time interval (first time window of the successive time interval) that includes the eleventh day since incubation. The inventors also found that this signal, which is probably the heart beat of the embryo, increases in amplitude during the following days of incubation (second time window of the successive time interval). Examples for the dynamics in the intensity variation of the radiation response are described more specifically further below with reference to experiments conducted by the inventors.

Alongside the analysis of the measured data, and depending on the results of analysis, the identifier 1D outputs data indicative of each egg/embryo condition in the different regions of interest, to be exploited by the environmental controller if a need for changing the environmental conditions arises.

Figure 1C:
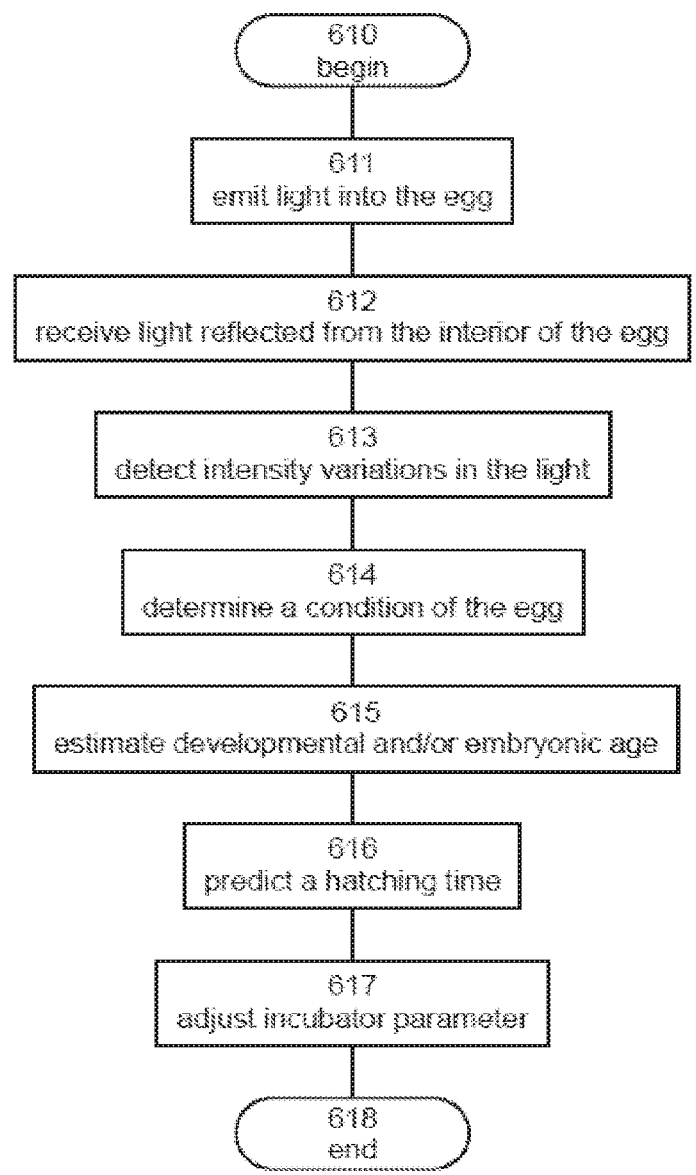
FIG. 1C is a flowchart diagram of an example of the method of the invention suitable for examining an egg.

Referring now to FIG. 1C, there is shown a flowchart diagram of a method suitable for examining an egg according to various exemplary embodiments of the present invention. The method begins at 610 and continues to 611 at which light from a light source is emitted into the egg. The light is optionally and preferably monochromatic light. In some embodiments of the present invention an infrared (IR) light (e.g., near IR, short IR, mid IR) is employed. In some embodiments visible light, optionally and preferably red light, is employed. Preferred wavelength range for the light is from about 600 nm to about 8000 nm, or from about 600 nm to about 3000 nm, or from about 600 nm to about 1550 nm, or from about 750 nm to about 1400 nm.

In various exemplary embodiments of the invention the emission of the light is executed in pulses, where no light is emitted between successive pulses. Use of pulses is advantageous because it allows operating the light source at elevated power. Use of pulses is also advantageous during light detection as further detailed below. In embodiments in which light is emitted in pulses the characteristic duration of a single pulse is typically less than 30 µs, or less than 25 µs, or less than 20 µs, or less than 15 µs. The characteristic duty cycle of each pulse (ratio between the period during which light is emitted and the period during which light is not emitted) is from about 5% to about 50%.

The method continues to 612 at which light reflected from the interior of the egg is received. The light can be received by a light sensor configured to detect light at the wavelength(s) of the emitted light and produce an electrical signal responsively to the detection. When the light is emitted in pulses, the light sensor is optionally and preferably also operated when no light is emitted. The advantage of this embodiment is that it allows determining the characteristic level of the dark current of the sensor, and subtracting the signal corresponding to the dark current from the generated signal. Preferably, at least one dark reading is executed before or after emission of each pulse.

In some embodiments of the present invention the light source and the light sensor both are separated from the egg by an air gap, such that the egg is on one side of the air gap and both the light source and the light sensor are on an opposite side of the air gap. Thus, the present embodiments contemplate contact-free examination wherein the examination devices (light source, light sensor) do not contact the egg during the examination. In some embodiments of the present invention the examination of the egg is executed without attaching to the egg any solid object other than an egg holder supporting the egg from below.

The light source and light sensor are optionally and preferably either above or below the egg. When the light source and light sensor are above the egg, the air gap that separates them from the egg is above the egg, and when the light source and light sensor are below the egg, the air gap that separates them from the egg is below the egg.

Embodiments in which the light source and light sensor are above the egg are preferred from the stand point of examination accuracy, because in this configuration the emitted light can interact with an aircell within the egg. Embodiments in which the light source and light sensor are below the egg are preferred from the stand point of compactness since it allows simultaneous examination of eggs in vertically aligned trays. In these embodiments, the emission and receiving of the light is executed from below for an egg that is in the upper tray, and from above for an egg in the lower tray.

One of the advantages of having both the light source and the light sensor located on the same side of the egg (optionally and preferably without contacting the egg) is that an emission-sensing system having a light source and a light sensor can be easily deployed inside the incubator, for example, between adjacent trays in a vertical alignment configuration. Such deployment allows the method of the present embodiments to be executed in situ, while the egg is in an incubator. It is recognized by the present inventors that pulling the egg for examination outside the incubator is oftentimes undesired, particularly at the early days of incubation (e.g., before the tenth day of incubation, for chicken eggs), since in this period the embryo is more sensitive to changes in the environmental condition.

While examination of the egg in situ is preferred, some embodiments of the present embodiments contemplate examination of the egg outside the incubator. In these embodiments, the examination is optionally and preferably executed nearby the incubator (for example, at the same room in which the incubator is positioned). This is advantageous over manual techniques wherein, for the purpose of candling, the egg is first transferred to a dark room, which is remote to the incubator.

The method optionally and preferably continues to 613 at which periodic intensity variations in the light are detected.

As used herein, the term "periodic intensity variations" refers to variations in the intensity of the light over time in a repetitive manner a multiplicity of times, e.g., at least 10 times or at least 100 times or 1000 times or 10,000 times or more.

Periodic intensity variations can be detected by receiving a signal from the light sensor and analyzing the frequency content of the signal, which frequency content corresponds to periodic intensity variations in the received light. The detection is optionally and preferably performed by a signal and data processor that receives the signal and analyzes the signal to extract its frequency content. Preferably, the method also samples the signal, for example, at a sampling frequency of at least 100 Hz or at least 500 Hz. e.g., 1 kHz or more, in which case a digital analysis of the signal is executed.

The signal and data processor can be placed in the same encapsulation with the light source and light sensor, or it can be placed in another location nearby or remotely to the light source and light sensor. In the latter embodiment, the method transmits signals from the sensor to the signal and data processor over a communication network. The advantage of having the signal and data processor placed in another locations is that in such a configuration the signal and data processor can receive signals from a multiplicity of sensors that receive light from a multiplicity of eggs (e.g., one light sensor for each examined egg), so that simultaneous examination of a plurality of eggs can be performed. Also contemplated are embodiments in which part of the processing is performed by a circuit that is in the same encapsulation with the light source and light sensor, and part of the processing is executed by a circuit at a remote location. For example, the sampling can be executed by a circuit adjacent to the light sensor, and a digital signal can be transmitted, over a communication network, to circuit at a remote location for further processing.

In various exemplary embodiments of the invention the method determines the presence or absence of periodic variations in the light at a frequency of less than a threshold frequency $f_0$, wherein $f_0$ is 0.8 Hz or 0.7 Hz or 0.6 Hz or 0.5 Hz. In some embodiments, the method determines the presence or absence of periodic variations at a frequency from about 0.2 Hz to about 0.4 Hz, e.g., 0.3 Hz.

The method continues to 614 at which a condition of the egg is determined based, at least in part, on the presence or absence of the periodic variations in the light. It was unexpectedly found by the present inventors that periodic variations at low frequencies precede other periodic variations (such as, for example, periodic variations at frequencies of 3-4 Hz that are known to be associated with the heart beats of the embryo), and are therefore useful for determining the condition of the egg at early stages of the incubation. Without being bound to any particular theory, it is assumed that such low frequency variations are associated with the breathing cycle of the embryo in the egg.

In various exemplary embodiments of the invention the method determines the condition of the egg based on the presence or absence of the low-frequency (less than $f_0$) variations when the egg is at an age of from about 6 days to about 11 days. These embodiments are particularly useful when the egg is a chicken egg.

Conventional egg testing techniques that are based on heart beat frequencies typically employ analog high pass filtering or band pass filtering so as to filter out any frequency other than 2-3 Hz, thereby to maintain only variations associated with the heartbeat. It is recognized that in chicken eggs the detectable heart heat frequencies typically appear at or after the tenth or twelfth day of incubation. Thus, conventional automatic techniques are unable to determine the condition of the egg, particularly whether or not there is a live embryo in the egg, prior to the twelfth day of incubation.

Unlike conventional techniques, the method according to some embodiments of the present invention uses an unfiltered version of an analog signal indicative of the received light so that the low-frequency (less than $f_0$) variations can be detected, when present.

The determined condition of the egg is typically, but not exclusively, according to the classification of egg conditions as known in the art of poultry eggs. For example, the following classification can be employed. The condition of the egg can be referred to as "live" when the egg has a viable embryo. The condition of the egg can be referred to as a "clear" or "infertile" when the egg does not have an embryo. The condition of the egg can be referred to as "early dead" when the egg has an embryo which died at about one to seven days old. The condition of the egg can be referred to as "mid-dead" when the egg has an embryo which died at about seven to fifteen days old. The condition of the egg can be referred to as "late-dead" when the egg has an embryo which died at about fifteen to nineteen days old. The condition of the egg can be referred to as "empty" when a substantial portion of the egg contents are missing, for example, where the egg shell has cracked and the egg material has leaked from the egg. The condition of the egg can be referred to as "rotted" when the egg includes a rotted infertile yolk (for example, as a result of a crack in the egg's shell) or, alternatively, a rotted, dead embryo. While an "early dead", "mid-dead" or "late-dead egg" may be a rotted egg, those terms as used herein refer to such eggs which are not rotted. Infertile, empty early-dead, mid-dead, late-dead, and rotted eggs may also be categorized as "non-live" eggs because they do not include a living embryo.

When no light intensity variations are detected from the egg, the method can determine that the egg is infertile, empty or rotten. When light intensity variations are detected, the method can determine that the egg is live. When previously detected the light intensity variations disappear, the method can determine that the egg is early dead, mid-dead, late-dead or rotten.

In some embodiments of the present invention the method continues to 615 at which the developmental and/or embryonic age of an embryo in the egg is estimated based on appearance and disappearance of the variations. For example, for a chicken egg, when the method identifies the onset of periodic low-frequency (less than $f_0$) variations, the method can estimate that the developmental age of the embryo is about 6 days. When the method identifies disappearance of these periodic low-frequency (less than $f_0$) variations, together with an appearance of periodic variations at higher frequencies (e.g., from about 2 Hz to about 4 Hz), the method can estimate that the developmental age of the embryo is about 11 days. On the other hand, when the method identifies the disappearance of periodic low frequency (less than $f_0$) light intensity variations without the appearance of periodic variations at higher frequencies, the method can determine that the condition of the egg is mid-dead.

The present inventors discovered several stages of embryonic development that can be identified according to some embodiments of the present invention. An onset of a first stage is characterized by the appearance of periodic low-frequency (less than $f_0$) variations. An onset of a second stage is characterized by the gradual disappearance or blurring of the low-frequency signal. An onset of a third stage is characterized by a significant increment of amplitude for periodic variations of a higher frequency (about 3-4 Hz) which is characteristic for the heartbeat of the embryo. An onset of a fourth stage is characterized by a further increment of the amplitude for the periodic variations of the higher frequency. The present inventors found that for chicken eggs, the onset of the first stage typically occurs at day 6-7 of the incubation, the onset of the second stage typically occurs at day 11-12 of the incubation, the onset of the third stage typically occurs at day 15 of the incubation, and the onset of the fourth stage typically occurs at day 17 of the incubation.

According to some embodiments of the invention the method detects malposition and/or malformation of an embryo in the egg, based on the variations. This is optionally and preferably by identifying abnormalities in the measured vibrations. The present inventors found that malposition and malformation of the embryo in the egg are manifested by a detectable change in the measured variation pattern compared to measured variation for a normal embryo in a normal egg. Thus, according to some embodiments of the present invention the abnormalities in the measured vibrations are identified by comparing the measured vibrations to reference variations and determining the existence or absence of abnormalities based on the comparison. As demonstrated in the Examples section that follows, the present inventors were able to identify malposition of the type beak above right wing, and malformation of the type of exposed brain, based on the identification of abnormalities in the measured signal.

It is expected that other types of malposition and malformation types also generate detectable abnormalities in the measured variations, which abnormalities can be used to identify that the embryo is in a state of malposition and malformation. It is additionally expected that different types of malposition and malformation types generate different detectable abnormality patterns. Thus, in some embodiments of the present invention the method also identify the type of malposition and/or malformation, based on the detected abnormality pattern. This can be done by comparing the detected abnormality pattern to a reference abnormality pattern, for example, by accessing an annotated library of abnormality pattern and comparing the detected pattern to the patterns in the library, wherein the annotation closest match can be used for identifying the type of malposition and/or malformation.

Representative examples of malposition types identifiable according to some embodiments of the present invention include, without limitation, head between thighs, head in the small end of egg, head under left wing, head not directed toward air cell, feet over head, and beak above right wing.

Representative examples of malformation types identifiable according to some embodiments of the present invention include, without limitation, exposed brain, embryo without one or two eyes, embryo with more than two legs, deformed beak, no upper beak and deformed twisted leg.

In some embodiments of the present invention the method continues to 616 at which a hatching time of the egg is predicted based on appearance and disappearance of the variations. The hatching time can be predicted by the signal and data processor.

The hatching time can be done based on the estimated developmental and/or embryonic age of the embryo, for example, as determined at 615, and based on the total embryonic development period. For example, for a chicken egg, the total embryonic development period of a chicken embryo is 21 days, the method can predict the hatching time to be 15 days from the appearance of the low-frequency (less than $f_0$) variations. The prediction is optionally and preferably at a temporal resolution of one day or less (e.g., temporal resolution of 12 hours, or temporal resolution of 6 hours).

The method can optionally and preferably continue to 617 at which the incubator parameters (e.g., at least one of temperature, humidity, light conditions, gaseous content etc.) are adjusted so as to change (either advance or retract) the hatching time. The advantage of this embodiment is that a control over the hatching time of the eggs in the incubator can provide a narrower distribution of hatching times over a population of incubated eggs. This can improve the mortality of the hatchlings because the hatchlings are typically handled and treated collectively, so that when most of the eggs are hatched over a relatively short period of time, the variations in the response of the hatchlings to the handling and treatment are relatively small.

The method ends at 618.

Figure 2:
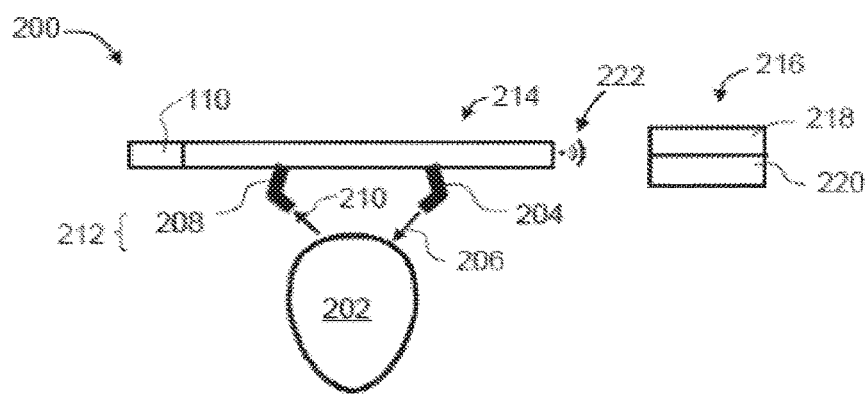
FIG. 2 is a schematic illustration of a system for examining an egg, according to some embodiments of the present invention.

Reference is now made to FIG. 2, which is a schematic illustration of a system 200 for examining an egg 202, according to some embodiments of the present invention.

System 200 can be used for executing at least a few of the operations described above with respect to FIGS. 1B and 1C.

System 200 comprises an optical unit including a light source 204 configured for emitting light 206 into egg 202, and a light sensor 208 (constituting a detection unit) configured for receiving light 210 reflected from the interior of egg 202 and for generating a signal indicative of received light 210. Light source 204 and light sensor 208 are collectively referred to herein as "an emission-sensing pair". System 200 can comprise more than one emission-sensing pair, so as to facilitate examination of more than one egg during a single measurement batch.

Source 204 preferably emits a monochromatic light. In some embodiments of the present invention an infrared (IR) light (e.g., near IR, short IR, mid IR) is employed. In some embodiments visible light, optionally and preferably red light, is employed. Preferred wavelength range for the light is from about 600 nm to about 8000 nm, or from about 600 nm to about 3000 nm, or from about 600 nm to about 1500 nm, or from about 750 nm to about 1400 nm. Source 204 may be, for example, a light emitting diode (LED). A representative example of a LED suitable for the present embodhiment is a High Power Infrared LED, part No. SFH 4550, OSRAM Opto Semiconductors GmbH Wernerwerkstrasse 2, D-93049 Regensburg, Germany.

Sensor 208 is preferably selected to be sensitive to the radiation emitted by source 204 in the sense that sensor 208 produces an electrical signal when radiation that has the parameters of the radiation emitted by source 204 impinges on sensor 208. Sensor 208 may be, for example, a photo diode. A representative example of a photodiode (PD) suitable for the present embodiments is a Silicon PIN diode. S6036 series, HAMAMATSU PHOTONICS K.K., Solid State Division, 1126-1 Ichino-cho, Higashi-ku, Hamamatsu City, 435-8558 Japan.

In some embodiments of the present invention, the optical unit is configured for contactless measurements: the source 204 and sensor 208 are separated from egg 202 by an air gap 212. As indicated above, the optical unit may be configured for optical measurements in either one of transmission and reflection modes (or both of them, by using for example two differently oriented detection channels associated with the common illumination channel). For example, the configuration may be such that egg 202 is on one side of air gap 212 and both source 204 and sensor 208 are on an opposite side of air gap 212. Air gap 212 is preferably a portion of the environment generally surrounding the egg, so that there is no additional encapsulation the contacts the egg during the emission and detection of the light. Light source 204 and light sensor 208 may be both above or below the egg 202 being monitored. In some embodiments, source 204 and sensor 208 are mounted on planar board(s) (e.g. circuit board(s)), preferable the same planar board 214. When system 200 comprises more than one emission-sensing pairs, two or more such pairs can be mounted on the same planar circuit board.

Figure 3:
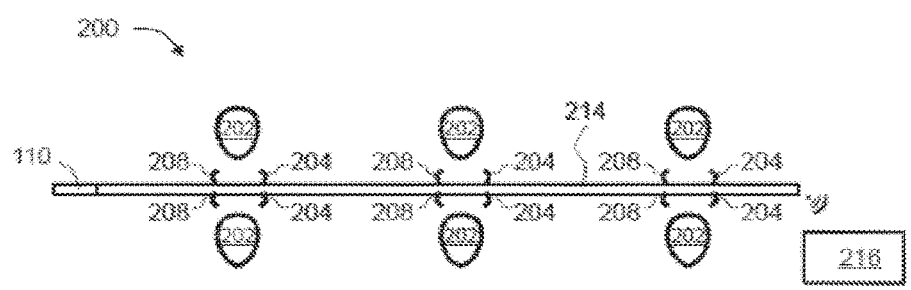
FIG. 3 is a schematic illustration of a system for examining an egg, in embodiments of the invention in which the system comprises more than one emission-sensing pair.

In the schematic illustration shown in FIG. 2 the circuit board 214 (including source 204 and sensor 208) is above egg 202, so that air gap 212 is above the egg. However, this need not necessarily be the case, since, for some applications, it may be desired to position source 204 and sensor 208 below the egg 202, as further detailed hereinabove. Further, the present embodiments also contemplated combination of embodiments in which system 200 comprises more than one emission-sensing pair (each including at least a light source and a light sensor), wherein at least one emission-sensing pair is above an egg in a lower tray and at least one emission-sensing pair is below an egg in an upper tray. This configuration is illustrated in FIG. 3. For clarity of presentation, the trays that hold the eggs are not illustrated in FIGS. 2 and 3.

System 200 preferable comprises a signal and data processor 216 (control unit) configured for determining a condition of the egg based, at least in part, on the signal received from sensor 208. Signal and data processor 216 can have an electronic circuit 218 and a non-volatile memory medium 220 readable by circuit 218, wherein memory medium 220 stores program instructions which, when read by circuit 218, cause circuit 218 to analyze the signal and extract its frequency content. Electronic circuit 218 can be dedicated circuitry or it can be an electronic circuit of a general purpose computer.

Preferably, the signal and data processor samples the signal, for example, at a sampling frequency of at least 100 Hz or at least 500 Hz, e.g., 1 kHz or more, in which case a digital analysis is executed. Alternatively, the sampling can be done by circuit 214 wherein processor 216 already receives a digital signal.

The signal and data processor can be placed in the same encapsulation with the light source and light sensor, or it can be placed in another location nearby or remotely to the light source and light sensor. In the latter embodiment, the signals from the sensor are transmitted to the signal and data processor over a communication network 222, which is illustrated as a wireless network but may also be a wired communication line.

The advantage of having processor 216 placed in another location is that in such a configuration the processor 216 can receive signals from a multiplicity of sensors that receive light from a multiplicity of eggs (e.g., one light sensor for each examined egg), so that simultaneous examination of a plurality of eggs can be performed.

In some embodiments of the present invention the signal from sensor 208 is received by processor 218 in an unfiltered form, and the extraction of frequency content is applied directly to the unfiltered signal. When sampling is executed by circuit 214, the sampling is preferably applied to the raw signal generated by sensor 208 without applying any analog filtering operation. These embodiments are particularly useful for determining the presence or absence of low-frequency components. Processor 216 optionally and preferably processes the signal to determine the present of absence of a periodic signal having a frequency of less than the threshold frequency $f_0$.

The term "periodic signal" is used herein to refer to a time varying signal having an oscillating waveform pattern which is repeated a multiplicity of times, e.g., at least 10 times or at least 100 times or 1000 times or 10,000 times or more. The time period over which the oscillating waveform pattern is repeated is preferably at least an hour or at least 6 hours or at least 12 hours or at least 24 hours or at least 48 hours, e.g., 72 hours or more.

Once the frequency content of the signal is obtained, processor determines the condition of the egg, and optionally also estimates the developmental and/or embryonic age of the embryo and/or predicts the hatching time, as further detailed hereinabove. Processor 216 preferably provides a sensible signal indication of information pertaining to the condition of the egg and/or the developmental and/or embryonic age of the embryo and/or hatching time of the egg. For example, processor 216 can display the information on a display device (not shown). When system 200 comprises a plurality of emission-sensing pairs, processor 216 optionally and preferably provides the information separately for each egg, associates the respective information with the respective egg, and provides an identification label (e.g., a serial number, a location within the incubator, etc.) that uniquely identifies the respective egg.

System 200 optionally and preferably comprises a controller 110 configured for operating light source 204 to emit light in pulses, as further detailed hereinabove. Controller may includes an electronic circuit and a non-volatile memory medium readable by the electronic circuit, wherein the memory medium stores program instructions which, when read by the electronic circuit, cause the electronic circuit to control the operation of light source 204. In the schematic illustration of FIGS. 2 and 3, controller 110 is shown on-board of circuit board 214, but this need not necessarily be the case, since, for some applications, it may not be necessary for the controller to be on-board. In some embodiments, controller 110 synchronizes the operations of source 204 and sensor 208. However, such synchronization may not be necessary since some embodiments of the present invention contemplate continues operation of sensor 208 so as to allow subtraction of dark readings from the signal generated by sensor 208. In these embodiments, controller 110 performs readings of signals from sensor 208 synchronously with emission of light by source 204, and subtracts the signal that correspond to the dark reading from the signal that is generated by sensor 204 in response to the received light. Preferably, controller 110 performs at least one reading that corresponds to dark current for each light pulse. When system 200 comprises a plurality of emission-transmission pairs, controller 110 optionally and preferably synchronizes between the operations of the various pairs so as to reduce cross-talks between signals that correspond to different eggs.

Figure 4:
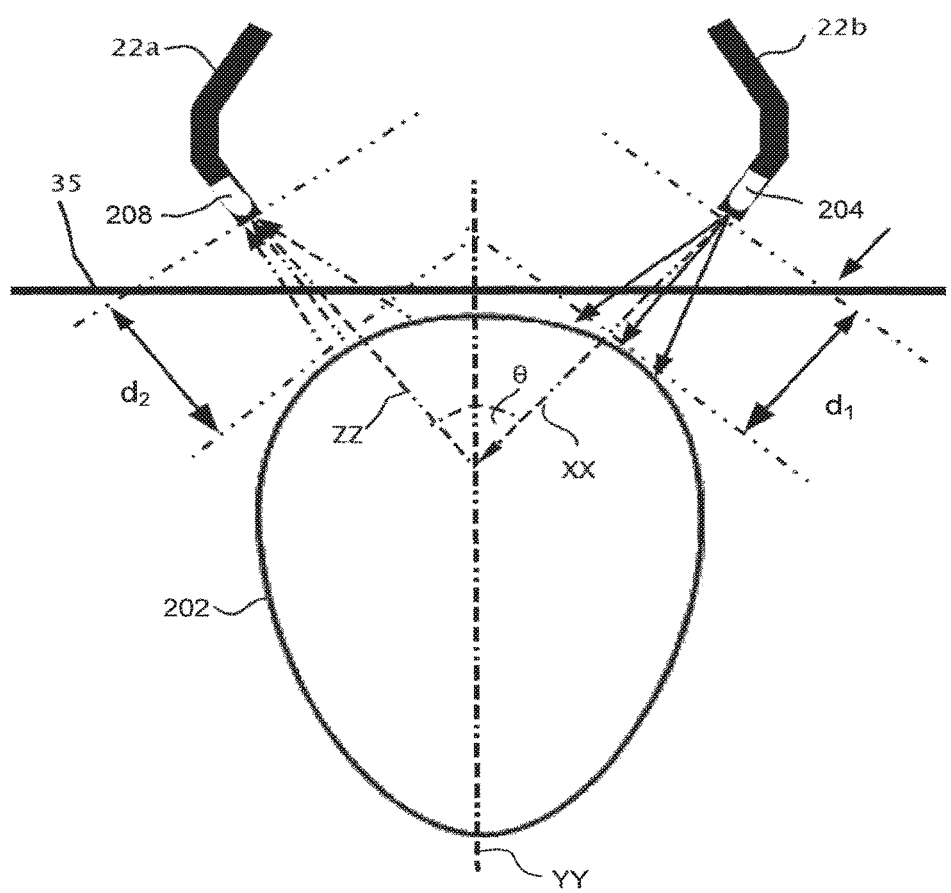
FIG. 4 is a schematic illustration of a relation between a light source, a light sensor and an egg, according to some embodiments of the present invention.

Reference is now also made to FIG. 4, which is a schematic illustration of a preferred relation between the light source, the light sensor and the egg. Egg 202 is illuminated with light source 204. Light source 204 is located in an arm 22b and light sensor 208 is located in an arm 22a. Arms 22a and 22b may be connected into a single housing corresponding to a single egg in an incubation tray, but may also be connected to a housing that correspond to a plurality of eggs, as illustrated in FIG. 3.

The center of the emitted beam of source 204 and the center of the field of view of reception of sensor 208 are shown in FIG. 4 by axes XX and ZZ respectively. Axis YY is shown as the longitudinal axis of egg 202 which is shown as substantially vertical. Arms 22a and 22b may be positioned such that there is an angle θ between axes XX and ZZ. The value of 0 can be from about 50 to about 120 degrees or from about 60 to about 110 degrees, or from about 70 to about 100 degrees. Illumination rays of egg 22 by source 204 are shown by arrows with solid lines and reflected light sensed by sensor 208 is shown by arrows with dotted lines. Although a single arrow of reflected light is shown, the reflected light entering and being sensed by sensor 208 may be singly or multiply scattered or reflected within egg 202.

Optionally and preferably arm 22b housing source 204 and arm 22a housing sensor 208 avoid contact with egg 202 and are separated from the shell of egg 202 by distances $d_1$ and $d_2$ respectively. The light intensity from source 204 may for examining egg 202 in the earlier stage of incubation may be less that the light intensity from source 204 used during later stage of incubation. The light level is optionally and preferably adjusted, for example, by controller 110 (not shown, see FIGS. 2 and 3) to avoid saturation in sensor 208. In some embodiments of the present invention an optical filter film 35 is placed between egg 202 and arms 22a and 22b. Optical filter film 35 may be absorptive, dichroic, monochromatic, infrared, ultraviolet, polarizing, guided, long-pass, short-pass, neutral density, bandpass or any optical filter known in the art.

Figure 5:
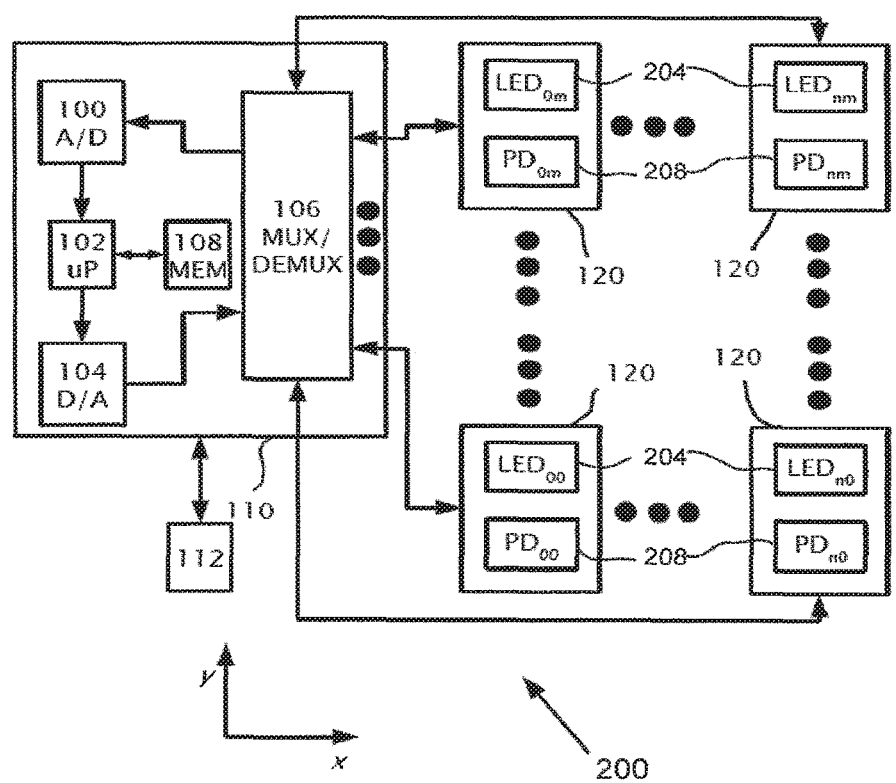
FIG. 5 is a simplified block diagram of the system in embodiments in which the system determines individually the condition of multiple eggs, according to some embodiments of the present invention.

Reference is now made to FIG. 5 which is a simplified system block diagram for system 200 in embodiments in which system 200 determines individually the condition of multiple eggs, according to some embodiments of the present invention. In the present embodiments system 200 comprises multiple sections 120 which respectively include multiple pairs of sources 204 and sensors 208 (shown as LEDs and PDs) corresponding to multiple eggs (not shown). Sections 120 can be in separate housings. In some embodiments at least two sections are in the same housing. Sections 120 are shown as arranged in a Cartesian array of n columns by m rows respectively, each source 204 is referenced as $LED_{nm}$ and each sensor 208 is referenced as $PD_{nm}$.

A controller 110 may include a microprocessor 102 which may access a read/write memory 108. System 200 may connect microprocessor 102 of monitor/control unit 110 via bidirectional signal lines to multiple sources 204 and sensors 208 via multiplexor (MUX)/demultiplexor (DMUX) 106. Microprocessor 102 is able to addressably access, send and/or receive a signal to specific sensor 208 and/or specific source 204 in system 200 by use of MUX/DMUX 106 controlled by microprocessor 102. Microprocessor 102 may receive input signals from multiple sensors 208 through an analogue to digital converter (A/D) 100. Output from microprocessor 102 to multiple sources 204 can be via a digital-to-analogue converter (D/A) 104. A serial interface 112 can also employed to connect to monitor/control unit 110 so as to connect an external computer system (not shown) for the purpose of configuring the operation of system 200.

Figure 6:
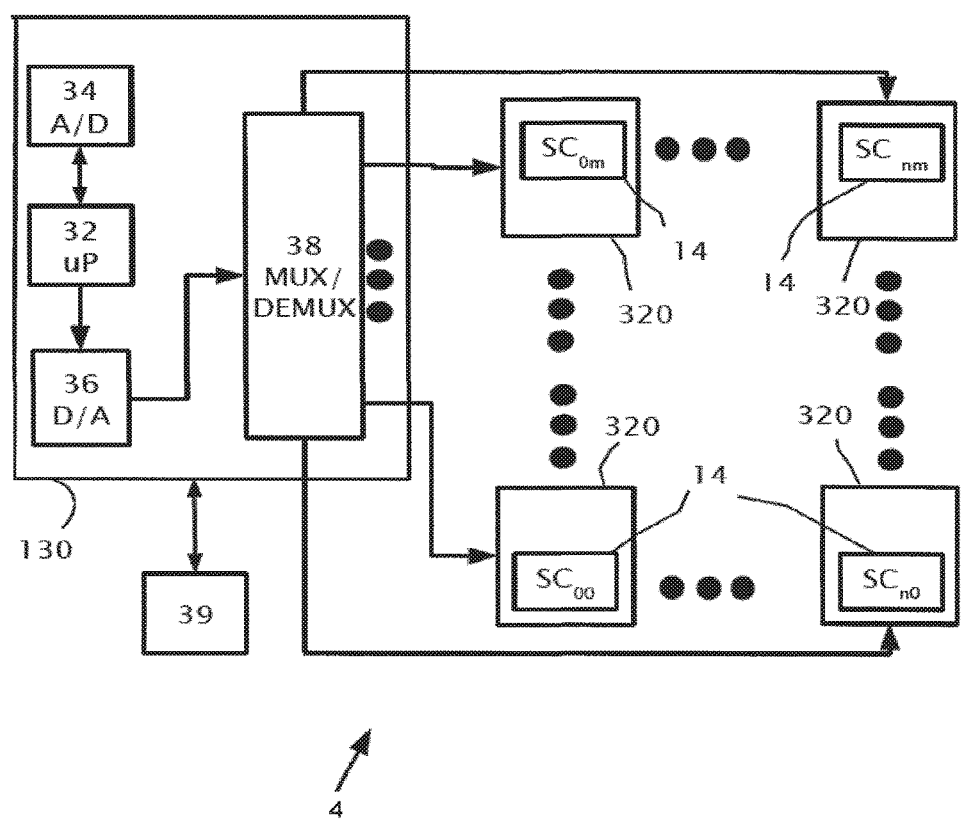
FIG. 6 is a simplified block diagram of an egg removal mechanism, according to some embodiments of the present invention.

Reference is now made to FIG. 6 which is a simplified system block diagram for removal mechanism 4 used to transfer eggs from an incubation tray to a hatching tray, according to some embodiments of the present invention. Removal mechanism 4 may include multiple actuators 320 and multiple suction cups 14. Actuators 320 may operate by selectively allowing or not allowing suction to suction cups 14. Actuators 320 may be arranged in an array of n columns by m rows respectively, each actuator 320 operates a corresponding suction cup 14 with four suction cups 14 shown with locations labeled by $SC_{nm}$. Removal mechanism 4 may connect to control unit 130 via bidirectional signal lines connected to the multiple suction cups 14 via multiplexor (MUX) 38. Microprocessor 32 is able to uniquely access and send a signal to a specific suction cup 14 in removal mechanism 4 by use of MUX 38 controlled by microprocessor 32. Access from microprocessor 32 to multiple suction cups 14 may be performed using multiplexor MUX 38 and digital to analogue converter (D/A) 36. A serial interface 39 may connect to control unit 130 so as to connect an external computer system for the purpose of configuring the operation of control unit 130. Microprocessor 32 may access read/write memory 108 which stores the locations of viable and/or non-viable eggs 6. Moreover, microprocessor 32 and microprocessor 102 may be the same microprocessor.

Figure 7:
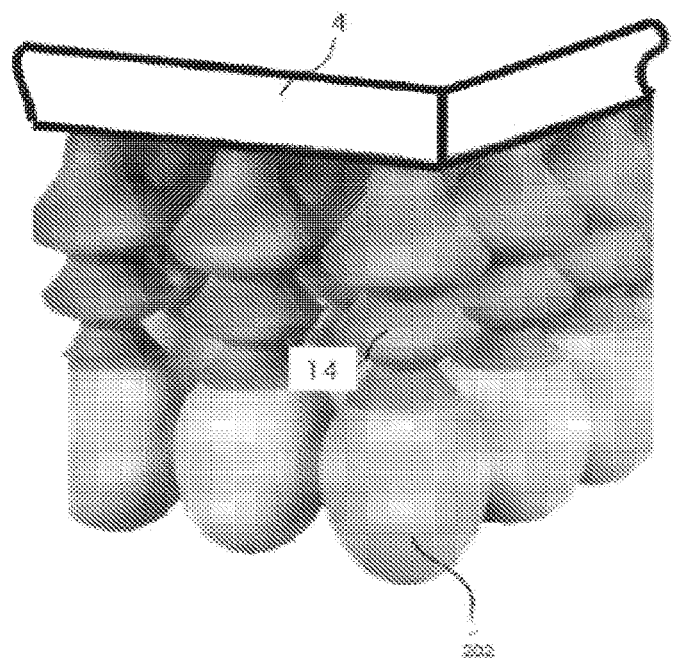
FIG. 7 is a schematic illustration of a partial isometric view of the egg removal mechanism, according to some embodiments of the present invention.

Reference is now made to FIG. 7 which schematically illustrates a partial isometric view of removal mechanism 4, according to some embodiments of the present invention. The partial isometric view shows eggs 202 held by suction cups 14 which may provide a vacuum to hold eggs 202 by suction. Particular eggs 202 may not be held by virtue of the vacuum not being applied to particular suction cups 14.

Figure 8:
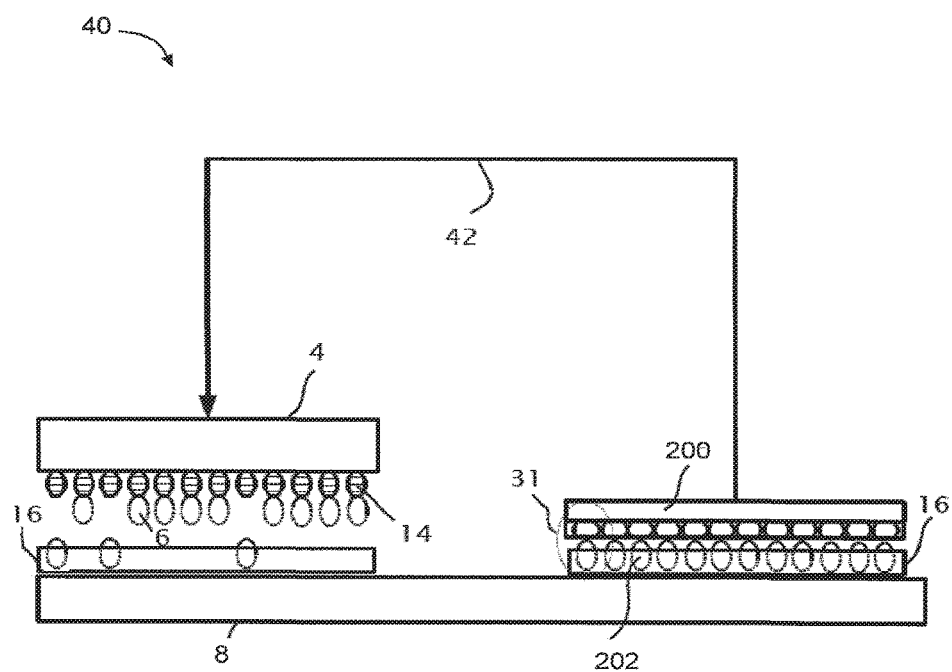
FIG. 8 is a schematic illustration of an egg handling system for the handling of eggs, according to some embodiments of the present invention.

Reference is now made to FIG. 8 which is a diagram of an egg handling system 40 for the handling of eggs 202, according to some embodiments of the present invention. System 40 shows a conveyer 8. An incubation tray 16 with eggs 202 is shown placed under examination system 200 which includes multiple sub-systems 31, each configured to examine one egg. Another incubation tray 16 is shown where a removal mechanism 4 has removed some viable eggs 6 from incubation tray 16 by use of actuators 14. Some of suction cups 14 may be activated so as to pick up viable eggs 6 and other suction cups 14 are not activated leaving non-viable eggs 6 in incubation tray 16. A data connection 42, optionally a wireless connection, may connect viability tester unit 2 and removal mechanism 4. The locations/tags of the viable and/or non-viable eggs 6 in incubation tray 16 may be passed via data connection 42 to removal mechanism 4 so that only viable eggs 6 are transferred to a hatching tray.

Figure 9A:
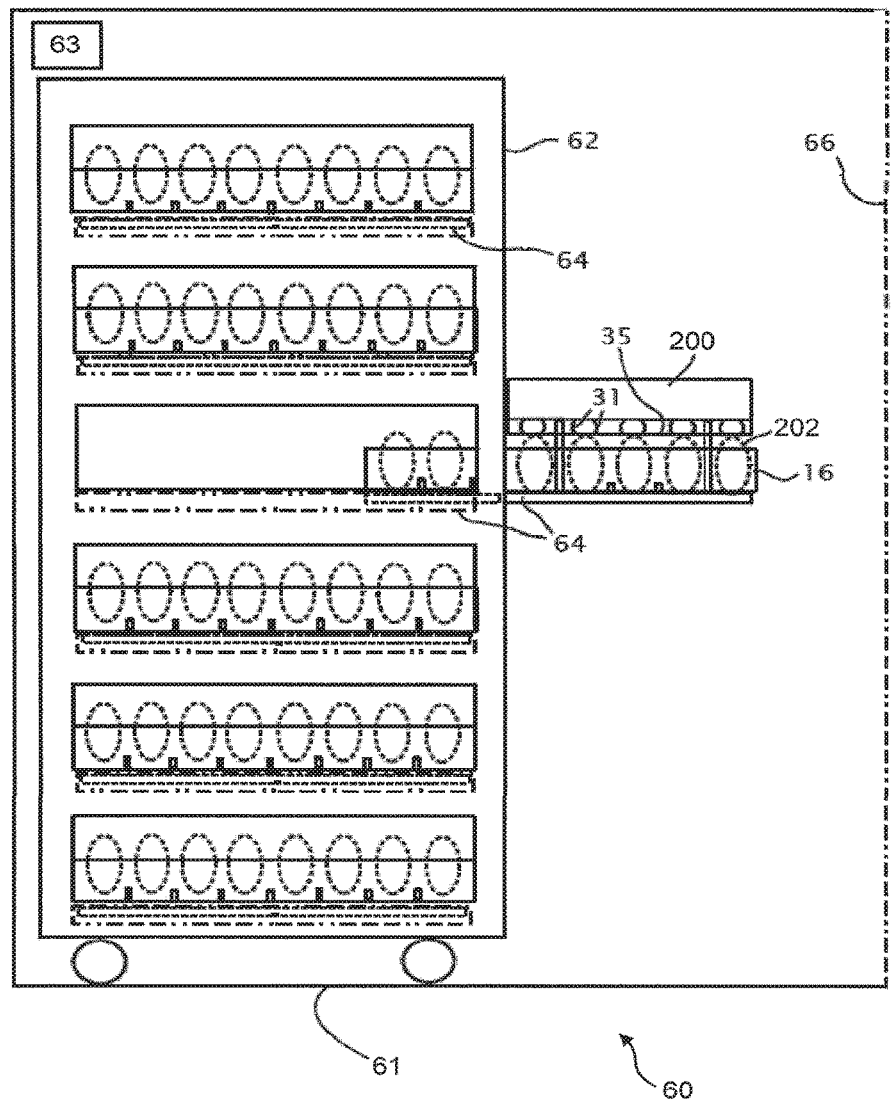
FIG. 9A is a schematic illustration of a side view of an incubator system, according to some embodiments the present invention.

Reference is now made to FIG. 9A which shows a side view of an incubator system 60, according to some embodiments the present invention. Incubator system 60 optionally and preferably has a housing 61 with an entrance door 66 which provides access to incubation trolley 62. A heater 63 is positioned in housing 61 so as to heat the interior of the housing. Heater 63 can include any known heating system that is suitable for heating an incubator housing. As a representative and non-limiting example, heater 63 can include a heat exchanger that removes heat from piping and releases and distributes the heat in the interior of the housing, as known in the art.

A number of incubation trays 16 are shown in situ. One incubation tray 16 is shown partially slid out on rails 64 to allow placement of examination system 200 above or below eggs 202. In some embodiments, system 200 may have rails in place such that incubation tray 16 when partially slid out on rails 64 allows placement of system 200 under eggs 200. System 200 is also shown with filter 35. System 200 may further include a wireless transmitter to a wireless local area network (WLAN), e.g., based on a standard of Institute of Electrical and Electronics Engineers' (IEEE) 802.11, to transmit the viability status of eggs 202 and their locations in incubation tray 16 to a nearby local area network (LAN). System 200 may include a button (not shown) to initiate a test of multiple eggs and an indicator (LED) (not shown) to initiate and confirm completion of a viability test of eggs 202.

Figure 9B:
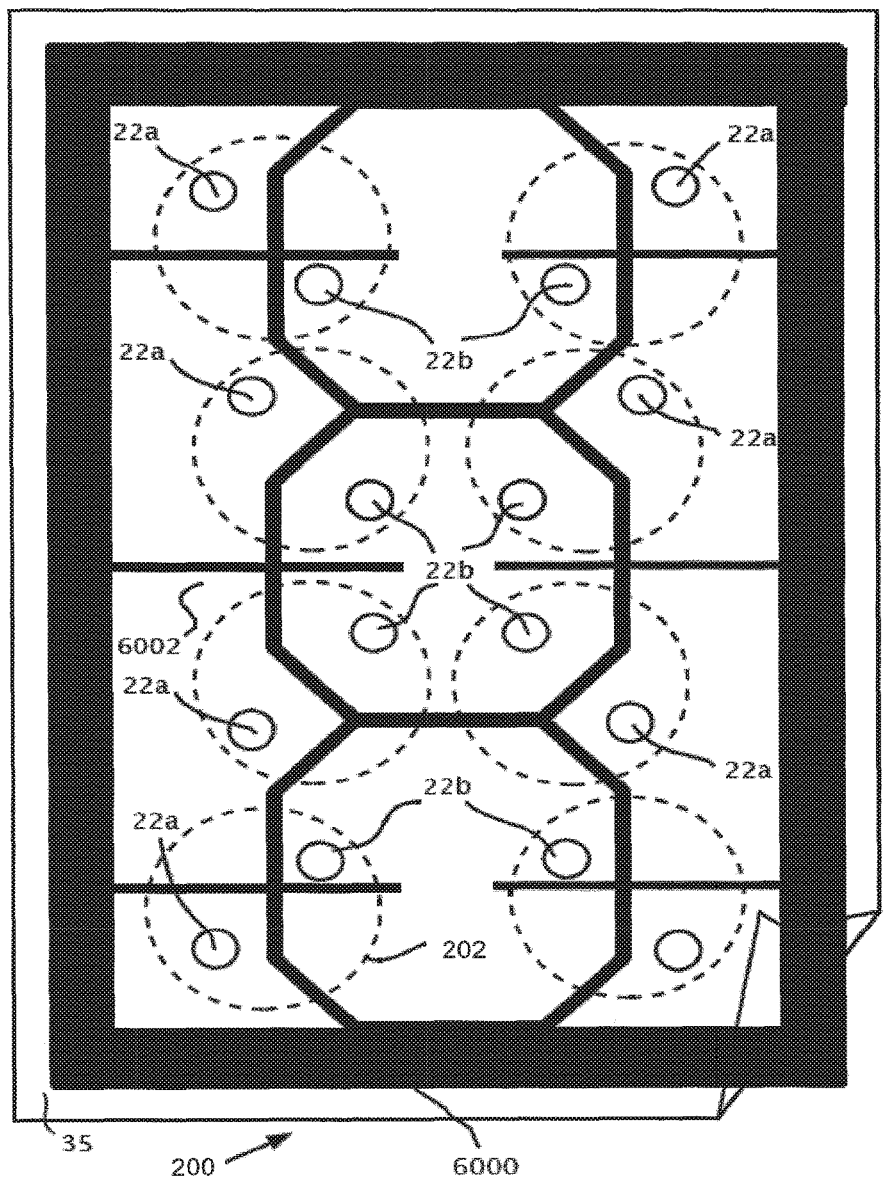
FIG. 9B is a schematic illustration of an upper view of the system for examining an egg, according to some embodiments of the present invention.

FIG. 9B is a schematic illustration of system 200, according to some embodiments of the present invention. System 200 includes a frame 6000 which provides a surface for the attachment of optical filter film 35 onto frame 6000. Set back from frame 6000 is back plane 6002 which is attached to and/or is an integral part of frame 6000. Back plane 6002 allows for the fixing and mounting of arms 22a and 22b. Positions of eggs 202 are shown with dotted lines relative to respective pairs of arms 22a and 22b. System 200 is not limited to eight eggs 202 as shown but may constructed to accommodate various numbers of eggs and incubation trays 16 capacities and/or dimensions.

Figure 10:
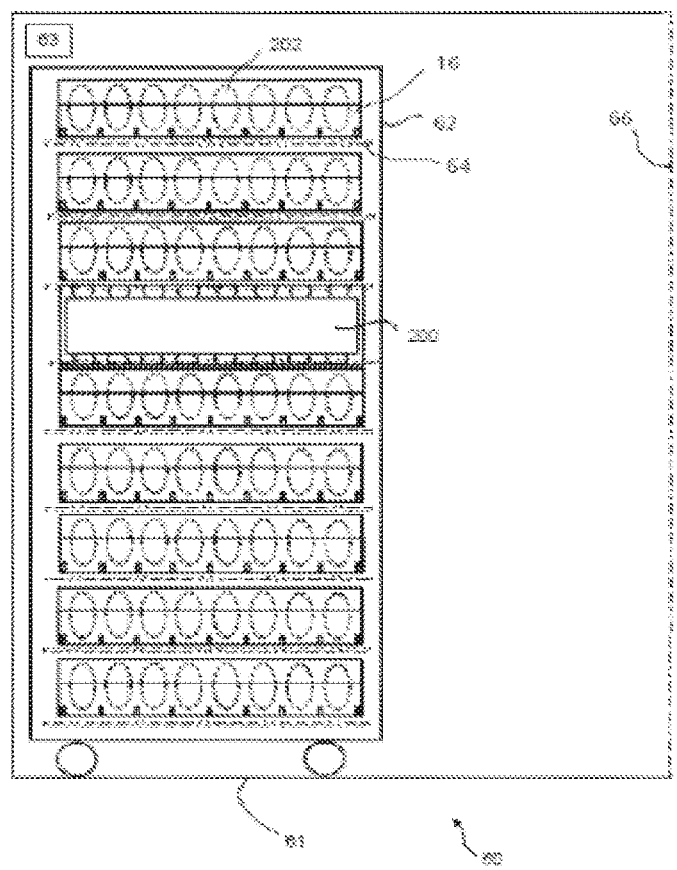
FIG. 10 is a schematic illustration of side view of the incubator system, according to additional embodiments of the present invention.
Figure 11A:
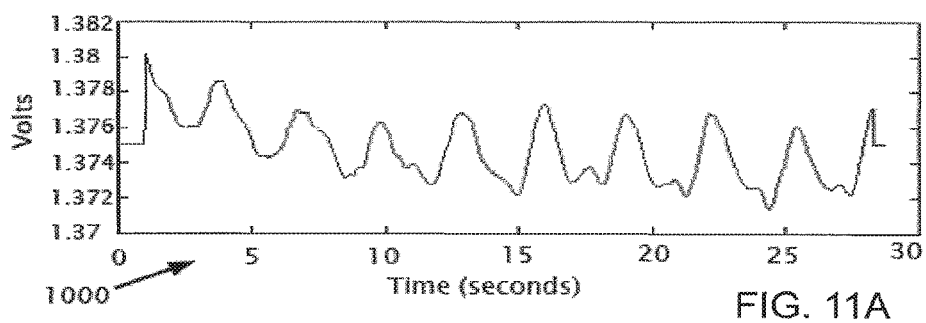
FIGS. 11A-H show graphs of voltage versus time (in seconds) for a chicken egg monitored in an incubation tray, obtained during experiments performed using an examination system according to some embodiments of the present invention.
Figure 11B:
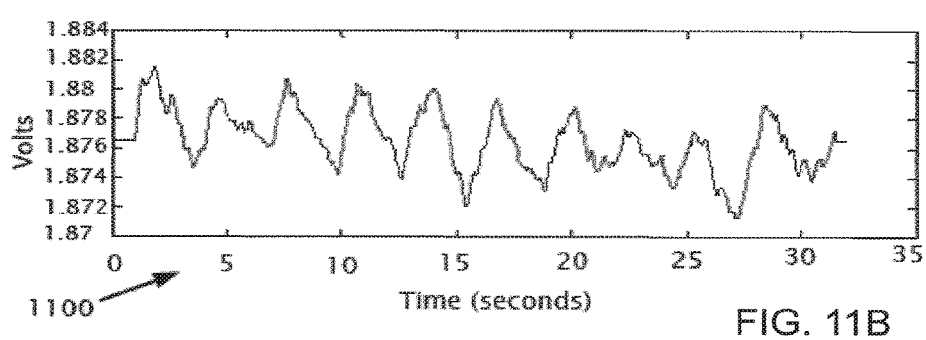
Figure 11C:
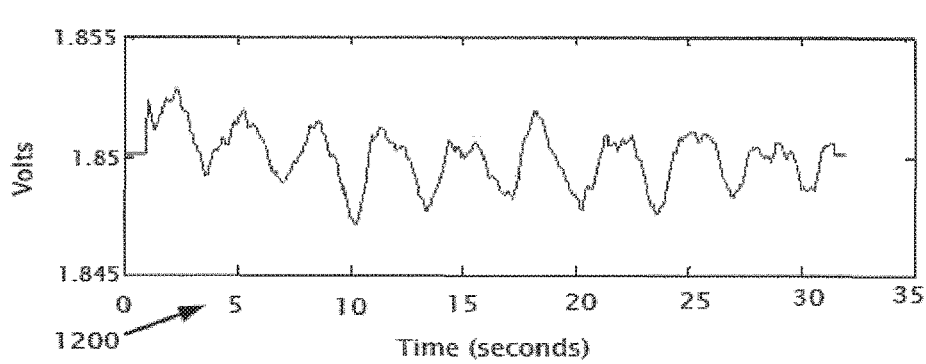
Figure 11D:
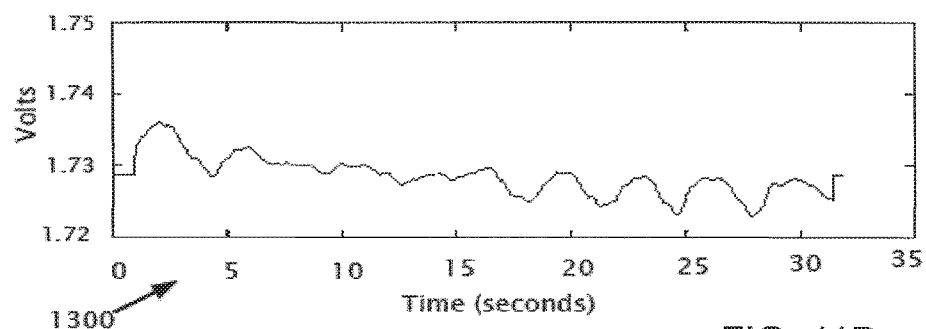
Figure 11E:
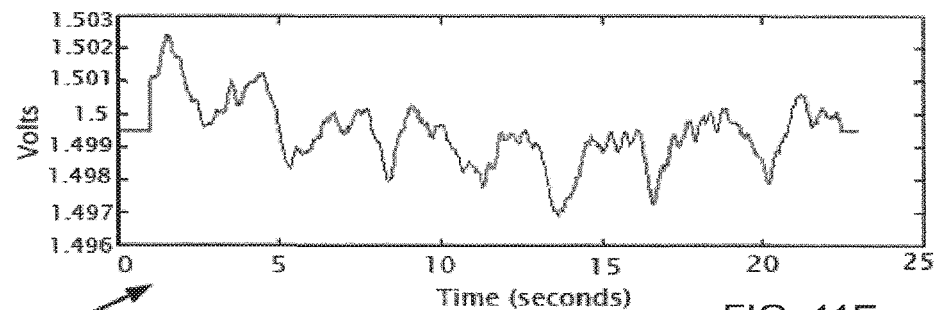
Figure 11F:
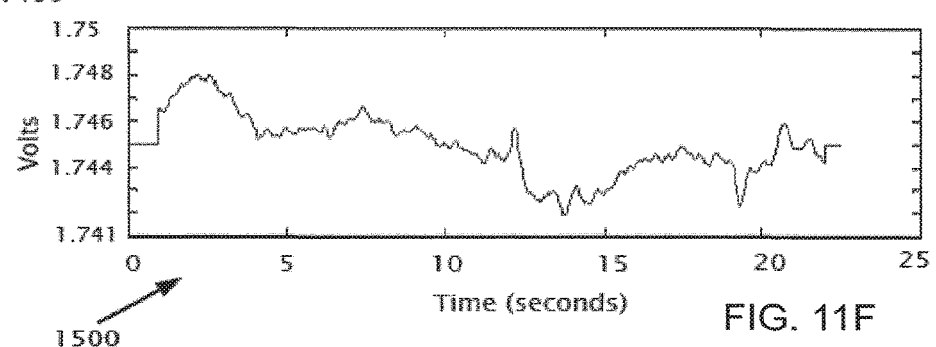
Figure 11G:
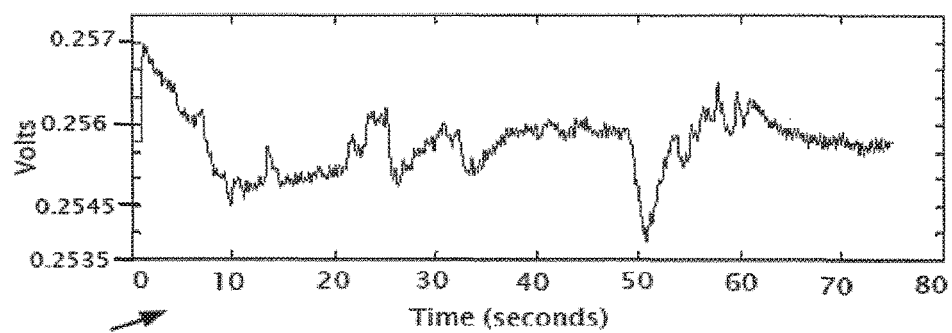
Figure 11H:
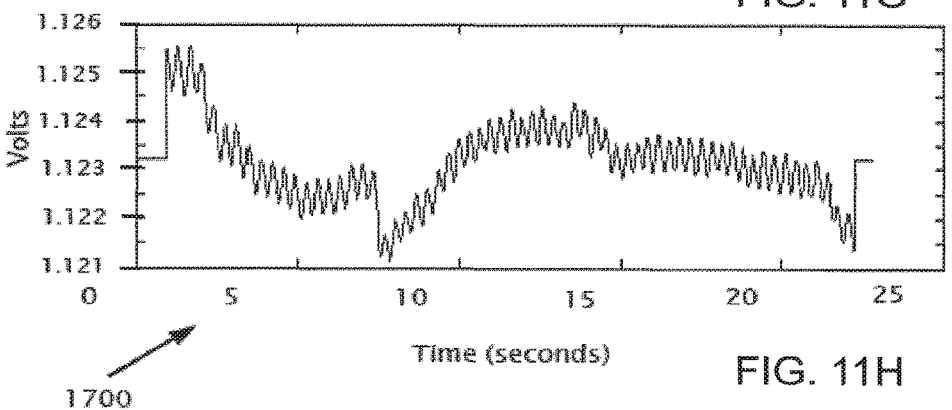

Reference is now made to FIG. 10 which is a schematic illustration of a side view of incubator system 60, according to some embodiments of the present invention. Incubator system 60 has entrance door 66 which provides access to incubation trolley 62. A number of incubation trays 16 are shown in situ. One incubation tray 16 is shown removed completely and replaced by examination system 200. In situ, system 200 is seen with sub-systems above the eggs in one incubation tray and with sub-systems below the eggs in another incubation tray 16. Alternatively, system 200 may be formed from two separate units placed back to back, one unit above the eggs in one incubation tray and the other unit below the eggs in another incubation tray 16. In some embodiments the emission-sensing pairs of system 200 are integrated to be part of an incubation tray 16 such that the top or bottom of the incubation tray 16 monitors the eggs in the incubation tray 16 as well as either the bottom of eggs in another incubation tray 16 above or another incubation tray 16 below respectively.

In some embodiments, instead of having system 200 in situ within incubator 60, system 200 are positioned in a different location so that possible areas within incubator 60 may be identified which did not provide optimal incubation conditions for the eggs located there.

It is expected that during the life of a patent maturing from this application many relevant incubation techniques will be developed and the scope of the term incubator is intended to include all such new technologies a priori.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. These examples illustrate the dynamics of the measured data (variation of the radiation response of the interior of the egg) obtained at different time intervals of the incubation period.

Example 1

Reference is now made to FIGS. 11A-H which show graphs of the electric output (voltage) of the optical sensor versus time (in seconds) for a chicken egg monitored in an incubation tray, using an examination system according to some embodiments of the present invention. FIGS. 11A-H represent typical graphs of monitored signals of chicken eggs for three empirically measured stages of embryonic development based on the monitored signals during incubation of chicken eggs in an incubator.

The first empirically measured stage (initial time interval of the incubation period) is when chicken eggs are placed in the incubator to approximately the time of the seventh day. Graph 1000 shows a monitored voltage signal for eggs 6 for a time period around the seventh day. In graph 1000 it can be seen that there are periodic signals of frequency between 0.1 and 0.4 Hertz which indicate live or viable chicks in the eggs. The absence of periodic signals around day seven are an indication of possible unfertilized eggs or eggs which have been fertilized but are not alive. Graphs 1100, 1200, 1300 and 1400 are typical graphs of voltage versus time for eggs monitored from day nine onwards which still indicate the periodic nature of signals which indicate live or viable chicks in the eggs.

A second empirically measured stage (first time window of a successive time interval) is around the time of the thirteenth day shown by graphs 1500 (FIG. 11F) and 1600 (FIG. 11G) and are indicative of a lack of periodicity in monitored signals of the eggs. However, monitored signals 1500 and 1600 are significantly changing apparently randomly in time which is indicative of viable eggs in an empirical stage of embryonic development.

A third stage (second time window of a successive time interval) begins around day seventeen where noticeable periodicity of higher frequency between 2 and 3 Hertz may be discerned in measured signals from chicken eggs as shown in graph 1700 (FIG. 11H) which correspond well to a heartbeat frequency.

Example 2

Figure 12A:
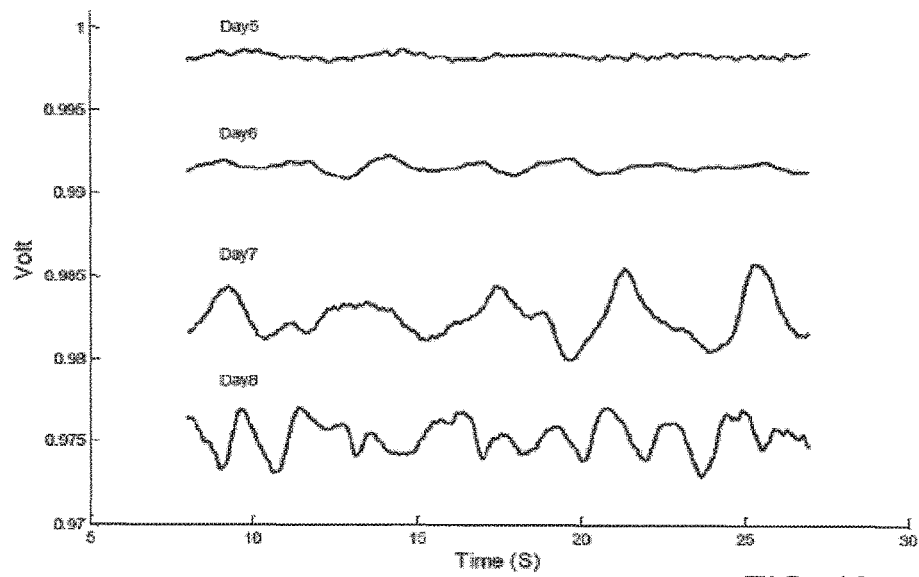
FIGS. 12A-D show further experimental results obtained during experiments performed using an examination system according to some embodiments of the present invention.
Figure 12B:
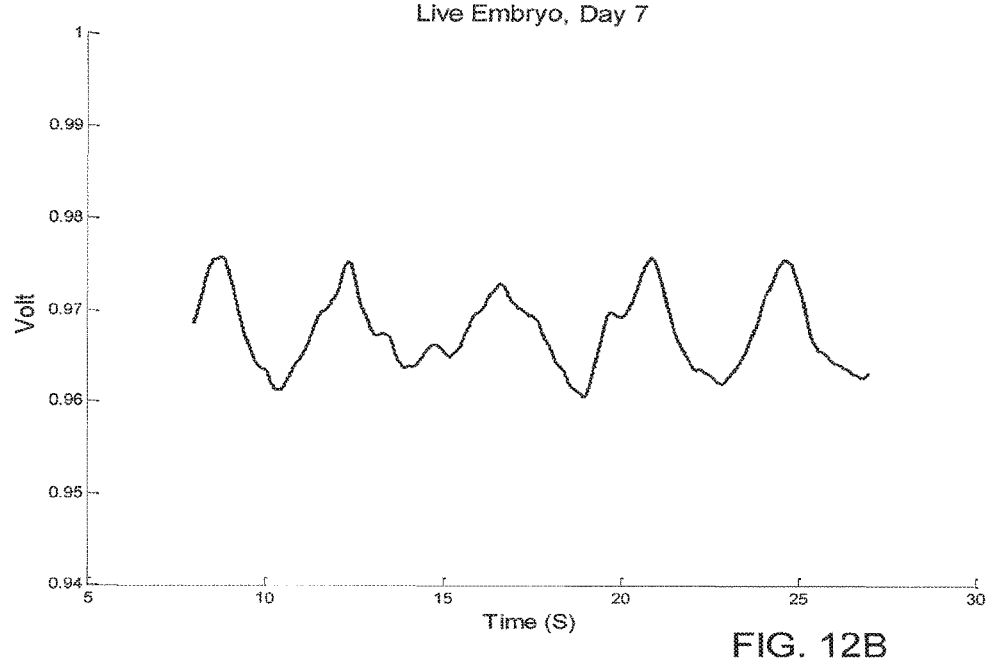
Figure 12C:
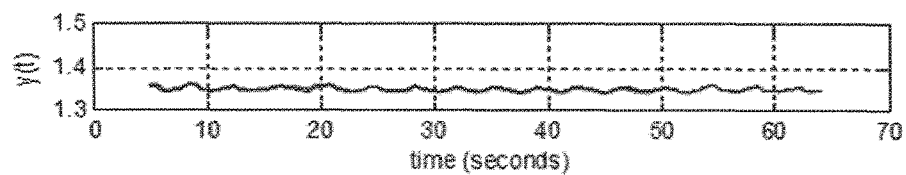
Figure 12D:
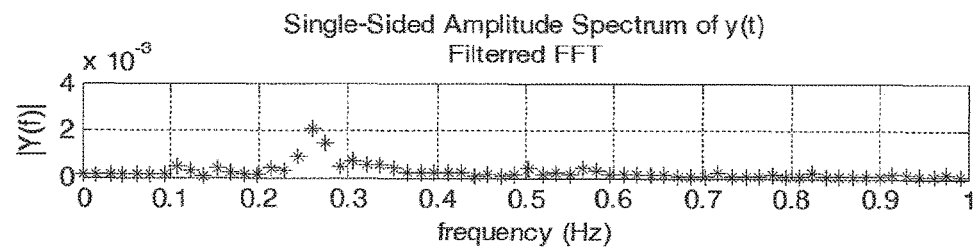

Reference is now made to FIGS. 12A-D, which show further results using an examination system according to some embodiments of the present invention. FIG. 12A shows relative voltage variation from signals of from a chicken egg versus time for each of the days 5-8 of the incubation period where, beginning at Day 6, a low frequency periodic variation 0.2-0.4 Hertz is seen in the waveforms. The amplitude of low frequency periodic variation is increased at Day 7 and Day 8. FIG. 12B is an enlarged view of a portion of the signal obtained during the 7th day. FIG. 12C shows a typical trace pattern for another chicken egg at day 7 showing amplitude variation y(t) versus time in seconds. FIG. 12D shows a single sided amplitude frequency spectrum of the signal of FIG. 12A shown as the modulus of amplitude variation |y(t)| versus frequency, where the distinctive alternating periodicity is identified as being between 0.2 to 0.3 Hertz. The absence of periodic signals around day seven are an indication of possible unfertilized eggs or eggs which have been fertilized but are not alive. Prior to days 5 no significant periodicity is has yet been observed.

Figure 13A:
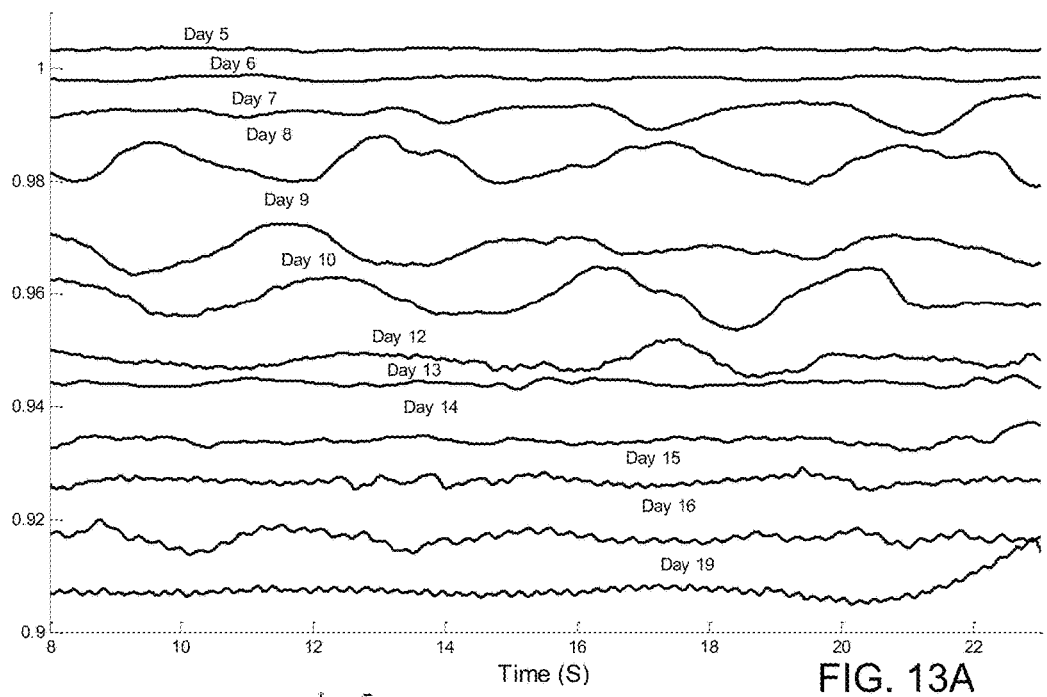
FIGS. 13A-B show further experimental results obtained during experiments performed using an examination system according to some embodiments of the present invention.
Figure 13B:
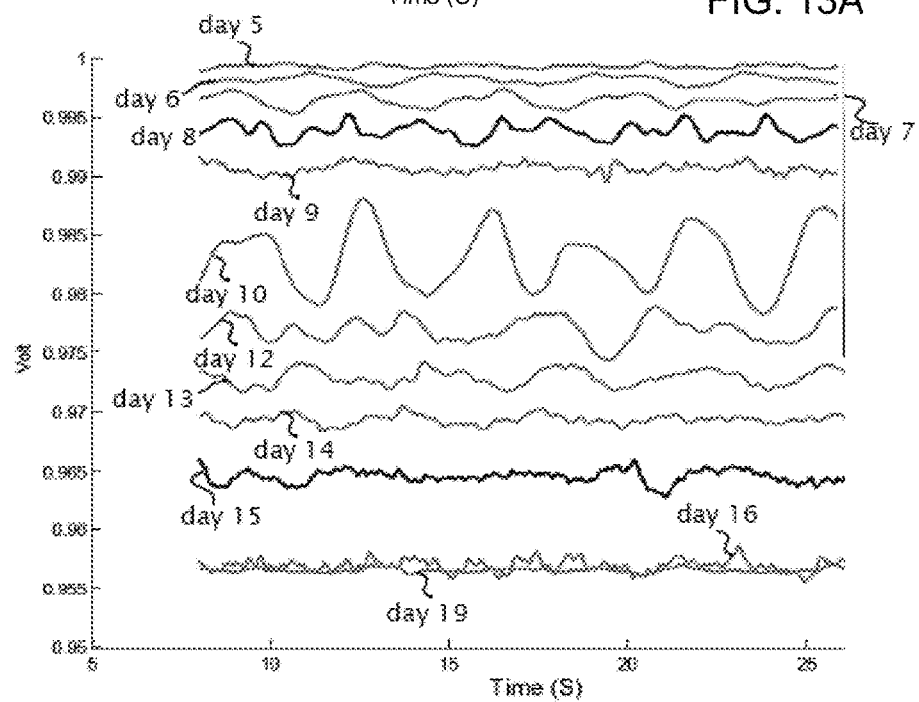

Reference is now made to FIGS. 13A and 13B which show further results using the egg examination system of the present embodiments. FIGS. 13A and 13B includes graphs of relative voltage variation from signals versus time for each of the days 5-10, 12-16 and day 19 for two different eggs. Both FIGS. 13A and 13B, the distinctive periodicity for days 5-8 of the incubation period (initial time interval), with the frequency component between 0.2 to 0.3 Hertz has disappeared around day 12. By days 15, 16 signals of FIG. 13A show increased amplitude of measured heart rate of approximately 4 Hertz or 240 heart beats per second. The embryo of FIG. 13A at day 19, appears alive and well. In the embryo of FIG. 13B, a malformation (exposed brain) occurred. This embryo, appears to have an erratic and weak heartbeat during days 15 and 17 during day 19 is apparently dead, as shown by the flat line.

Example 3

A comprehensive experiment has been performed according to some embodiments of the present invention, in a commercial hatchery at Kvutzat Yavne, Israel.

Methods

The experiment was performed in a multi stage incubator. Two groups of 64 eggs were marked in two incubation trays.

Group 1 included eggs from a hen flock 57 weeks of age, and group 2 included eggs from a hen flock 43 weeks of age. In the art of chicken eggs, incubation is usually performed for hen flocks having ages of from about 26 weeks to about 65 weeks. Thus, group 1 is considered an elder flock and group 2 is considered a central age flock. Since the eggs of group 2 were originated from a younger flock of hens, the eggs in this group were smaller in height.

The eggs in each group were numbered from 1 to 64, and the position of each egg was recorded and remained fixed during the experiment. Each egg was examined by the same light source and sensor during the entire experiment.

The eggs of group 1 were transferred to a hatcher at age 18 days, and eggs of group 2 were transferred to a hatcher at age 19 days. The eggs were transferred to hatching trays divided into cells so as to allow the association of each hatchling with a respective egg.

The light source was a LED that was activated by a current ranging from about 100 mA to about 600 mA. Each egg was examined for a period of about 60 seconds. The sampling frequency of the signal from the sensor was about 1 kHz. In group 1, examination was executed both from above and from below. In group 2, examination was only from above.

Table 1 below summarizes the experiment schedule, over three consecutive weeks.

TABLE 1

| Sat | Fri | Thu | Wed | Tue | Mon | Sun |
|---|---|---|---|---|---|---|
| no measurement | | | | | | group 1 (day 7) group 2 (day 5) |
| no measurement | no measurement | transfer group 1 end of experiment | hatching group 2 | | hatching group 1 | transfer group 2 |

Results

For live eggs, the obtained signals allowed distinction between four embryonic development stages, approximately at days 6, 12, 15 and 17. An onset of a first stage is characterized by the appearance of periodic low-frequency (less than 10) variations, typically at days 6-7. An onset of a second stage is characterized by the gradual disappearance or blurring of the low-frequency signal, typically at days 11-12. An onset of a third stage is characterized by a significant increment of amplitude for periodic variations of higher frequency (about 3-4 Hz) which is characteristic for the heartbeat of the embryo, typically at day 15. An onset of a fourth stage is characterized by a further increment of the amplitude for the periodic variations of the higher frequency, typically at day 17.

Figure 14A:
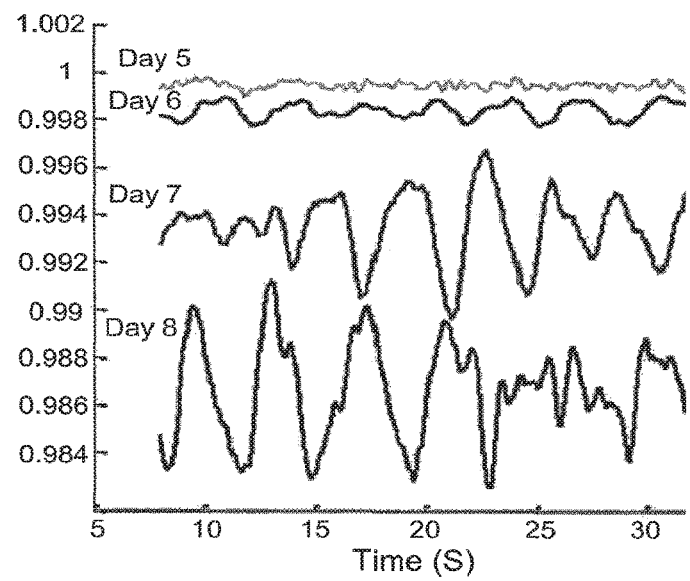
FIGS. 14A-C show signals from an egg with a live embryo, as obtained during an experiment performed using an examination system according to some embodiments of the present invention.
Figure 14B:
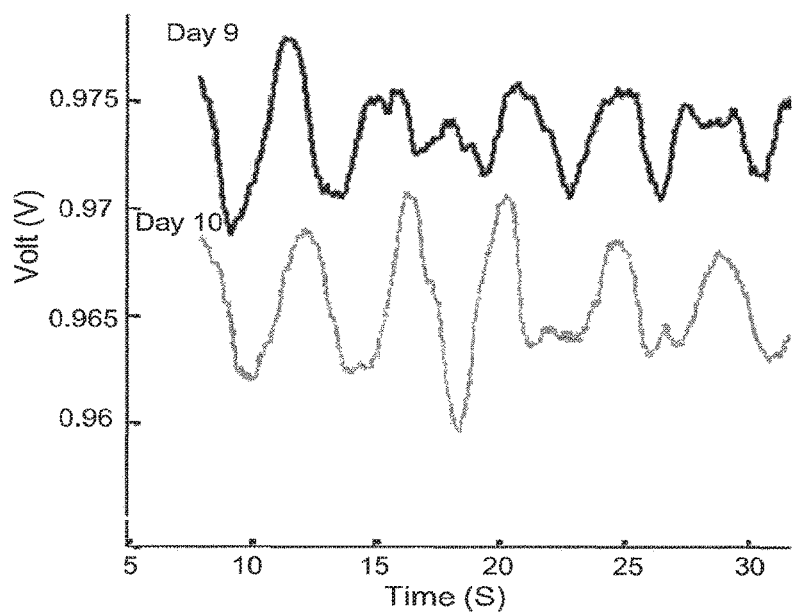
Figure 14C:
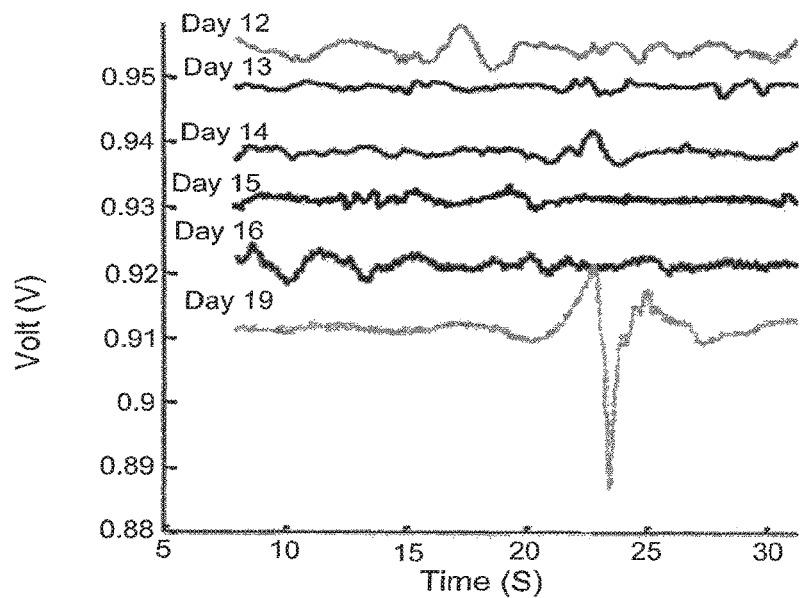

FIGS. 14A-C show signals from an egg from group 2 with a live embryo, as obtained during the entire experiment.

Figure 15:
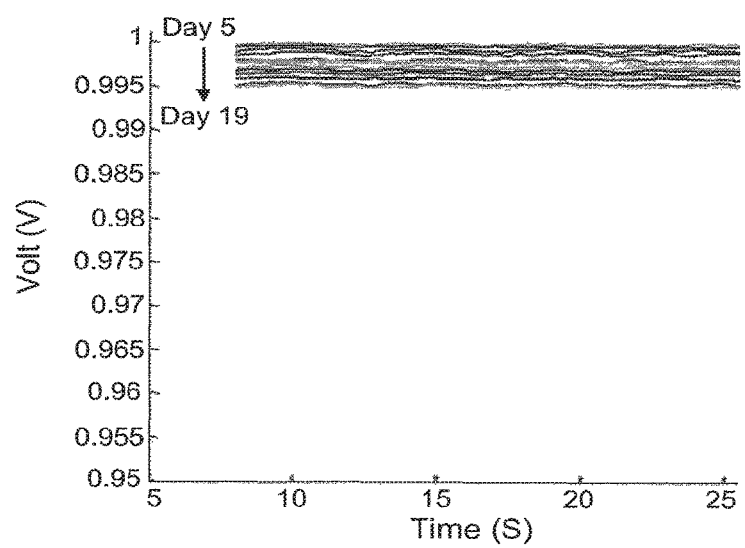
FIG. 15 shows signals from an empty egg, as obtained during an experiment performed using an examination system according to some embodiments of the present invention.

FIG. 15 shows signals from an empty egg from group 2, as obtained during the entire experiment. As shown, no variations of the signal variations were observed.

Figure 16:
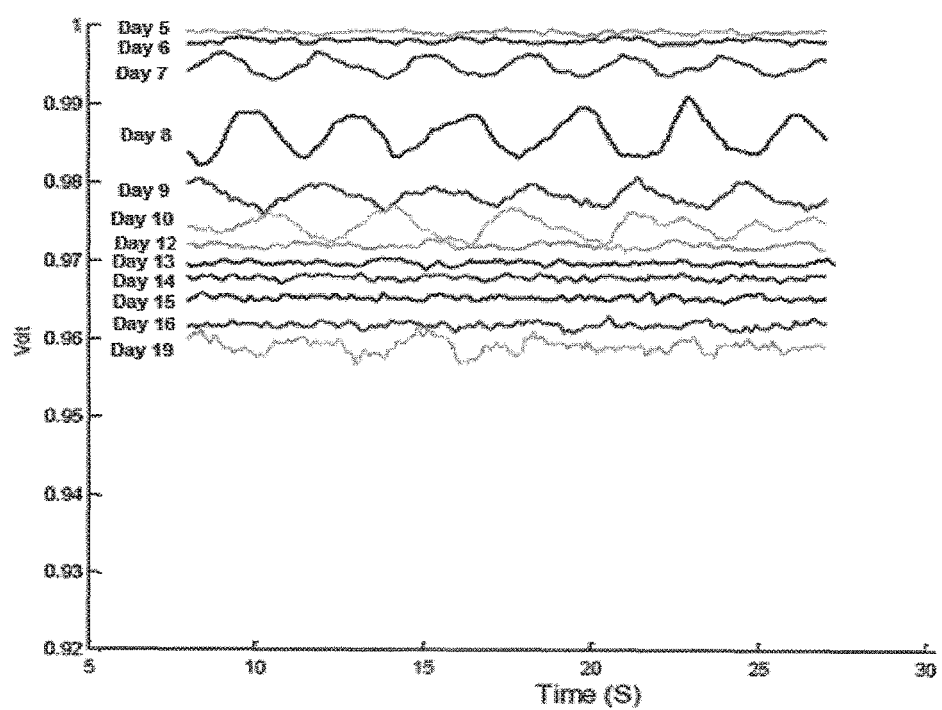
FIG. 16 shows signal from an egg in which a malposition (beak above right wing) occurred, as obtained during an experiment performed using an examination system according to some embodiments of the present invention.

FIG. 16 shows signal from an egg from group 2 in which a malposition (beak above right wing) occurred. The embryo was alive on the day of transfer but died on the day of hatching. As shown, the signal was abnormal on day 13.

The results for groups 1 and 2 are summarized in Tables 2 and 3, respectively. In Tables 2 and 3. M indicates a male hatchling and F indicates a female hatchling.

TABLE 2

| 1(F | 2 (M) | 4 infertile | 5(F) | 6(M) | 8(M) |
|---|---|---|---|---|---|
| 9(F) | 10(F) | 12 late death | 13(F) | 14(F) | 16(M) |
| 17(M) | 18(F) | 20(M) | 21(M) | 22 | 24(F) |
| 25(M) | 26(M) | 28(M) | 29(M) | 30 early death | 32(M) |
| 33(F) | 34 Infertile | 36(M) | 37(M) | 38(M) | 40(F) |
| 41 Early death | 42(M) | 44(F) | 45(F) | 46(F) | 48 Infertile |

TABLE 2-continued

| 49 Infertile | 50(M) | 52(M) | 53 Infertile | 54 late death | 56(M) |
|---|---|---|---|---|---|
| 57(F) | 58 early death | 60 | 61 | 62(M) | 64(F) |

Remarks:
Due to malfunctions in sensor Nos. 3 and 7, the respective eggs were not transferred.
In egg Nos. 20, 60 and 62, the hatchlings escaped from the cells and their gender was not determined.
Egg No. 41 was damaged on the 15th day.

TABLE 3

| 1(M) | 2(F) | 4(F) | 5(F) | 6 early death | 8 (M) |
|---|---|---|---|---|---|
| 9(F) | 10 hatchling escaped | 12 empty | 13(F) | 14(M) | 16 (M) |
| 17(M) | 18(F) | 20(M) | 21(M) | 22(M) | 24(M) |
| 25 empty | 26 empty | 28(M) | 29(M) | 30(F) | 32(F) |
| 33(F) | 34(F) | 36(M) | 37(F) | 38(M) | 40(F) |
| 41 empty | 42(M) | 44 abnormal signal observed (malformation) | 45(F) | 46(M) | 48(M) |
| 49(M) | 50(M) | 52(F) | 53(M) | 54 abnormal signal observed (malposition) | 56 Empty |
| 57(F) | 58(M) | 60(M) | 61(F) | 62 egg damaged | 64(M) |

Remakes:
Due to malfunctions in sensor Nos. 3 and 7, the respective eggs were not transferred.
In egg 44 there was no hatching due to a defect in the head. This was predicted by observing an abnormal signal on day 19.
In egg 54 the embryo was in a malposition state (beak above right wing) and the hatchling did not survived after hatching. This was predicted by observing an abnormal signal on day 13.

CONCLUSIONS

The system of the present embodiments successfully identified the viability of 100% of the eggs. The system of the present embodiments successfully identified death at early stages of incubation (at any day between day 7 and day 18).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. An incubator system, comprising:
   a housing for accommodating eggs at different sites in one or more trays;
   an optical system configured and operable to perform optical measurements over time on the eggs by applying illumination of a predetermined spectral range, detecting radiation responses from the eggs, and generating measured data indicative of dynamics in variations of the radiation responses of the eggs located at the different sites in said one or more trays during successive time intervals of an incubation process, said optical system being configured and operable to communicate said measured data to a control system; and
   an environmental controller configured and operable for monitoring various environmental conditions within the housing, said environmental controller being configured and operable for data communication with said control system to be responsive to control data from said control system to adjust the environmental conditions to optimize the incubation process and throughput.

2. An incubator system, comprising:
   a housing for accommodating eggs at different sites in one or more trays;
   an optical system configured and operable to perform optical measurements over time on the eggs by applying illumination of a predetermined spectral range, detecting radiation responses from the eggs, and generating measured data indicative of the radiation responses of the eggs located at different sites in said one or more trays during successive time intervals of an incubation process;
   an environmental controller configured and operable for monitoring various environmental conditions within the housing; and
   a control system configured and operable for communication with the environmental controller and for communication with the optical system to receive said measured data, the control system comprising a data processor configured and operable to analyze the measured data and determine a map of dynamics in variations of the radiation responses during the successive time intervals in the different sites, thereby enabling controllable adjustment of the environmental conditions to optimize the incubation process and throughput.

* * * * *